US007009041B1

(12) United States Patent
McDonough et al.

(10) Patent No.: US 7,009,041 B1
(45) Date of Patent: Mar. 7, 2006

(54) **OLIGONUCLEOTIDES FOR NUCLEIC ACID AMPLIFICATION AND FOR THE DETECTION OF *MYCOBACTERIUM TUBERCULOSIS***

(75) Inventors: Sherrol H. McDonough, San Diego, CA (US); Daniel L. Kacian, San Diego, CA (US); Nanibhushan Dattagupta, San Diego, CA (US); Diane L. McAllister, San Diego, CA (US); Philip W. Hammond, San Diego, CA (US); Thomas B. Ryder, Escondido, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 08/480,472

(22) Filed: Jun. 6, 1995

Related U.S. Application Data

(60) Division of application No. 08/345,861, filed on Nov. 28, 1994, now Pat. No. 5,766,849, which is a continuation of application No. 07/925,405, filed on Aug. 4, 1992, now abandoned, which is a continuation-in-part of application No. 07/855,732, filed on Mar. 19, 1992, now Pat. No. 5,399,491, which is a continuation-in-part of application No. 07/550,837, filed on Jul. 10, 1990, now Pat. No. 5,480,784, which is a continuation-in-part of application No. 07/379,501, filed on Jul. 11, 1989, now abandoned.

(51) Int. Cl.
*C07H 21/00* (2006.01)
*C12Q 1/68* (2006.01)
*C12P 19/34* (2006.01)

(52) U.S. Cl. ............... 536/23.1; 435/6; 435/91.2; 536/24.3; 536/24.33

(58) Field of Classification Search ............ 435/6, 435/91.21, 91.2, 91.53, 810; 536/24.33, 536/24.1
See application file for complete search history.

(56) References Cited

U.S. PATENT DOCUMENTS

| | | | |
|---|---|---|---|
| 4,683,202 A | | 7/1987 | Mullis |
| 5,030,557 A | * | 7/1991 | Hogan et al. ............. 435/6 |
| 5,130,238 A | | 7/1992 | Malek |
| 5,169,766 A | * | 12/1992 | Schuster et al. ......... 435/91 |
| 5,399,491 A | | 3/1995 | Kacian et al. |
| 5,422,242 A | * | 6/1995 | Young ..................... 435/6 |
| 5,521,300 A | * | 5/1996 | Shah et al. .......... 536/24.32 |
| 5,547,842 A | | 8/1996 | Hogan et al. ............. 435/6 |
| 5,554,516 A | * | 9/1996 | Kacian et al. ......... 435/91.21 |
| 5,906,917 A | * | 5/1999 | Hammond ................ 435/6 |
| 5,908,744 A | | 6/1999 | McAllister et al. |
| 6,150,517 A | | 11/2000 | Hogan et al. .......... 536/25.3 |

FOREIGN PATENT DOCUMENTS

| | | |
|---|---|---|
| CA | 559709 | 2/1988 |
| EP | 0300796 | 1/1989 |
| EP | 0329882 | 8/1989 |
| EP | 0398677 | 5/1990 |
| EP | 0373960 | 7/1990 |
| EP | 0408295 | 1/1991 |
| EP | 0439182 | 1/1991 |
| EP | 0461045 | 6/1991 |
| EP | 9207957 | 5/1992 |
| EP | 0587266 | 5/1993 |
| FR | 2651505 | 9/1989 |
| FR | 2659086 | 3/1990 |
| WO | 8706270 | 10/1987 |
| WO | WO-A-88 03957 | 6/1988 |
| WO | 8810315 | 12/1988 |
| WO | 8901050 | 2/1989 |
| WO | 9014439 | 11/1990 |
| WO | 9101384 | 2/1991 |
| WO | 9115601 | 4/1991 |
| WO | 9222663 | 12/1992 |
| WO | WO-A-93 04201 | 3/1993 |

OTHER PUBLICATIONS

Rogall et al., Journal of General Microbiology 136:1915-1920, 1990.*
Normand et al. Gene 111:119-124, 1992.*
Guatelli et al. P.N.A.S. 87:1874-1878, 1990.*
New England Biolabs Catalog [Published by New England Biolabs, Beverly, Mass., USA] pp. 60-63, 1987.*
Sommer et al., Nucleic Acids Research, vol. 17, No. 16, p. 6749, 1989.*
Boddinghaus et al., Journal of Chemical Microbiology, vol. 28, No. 8, pp. 1751-1759, 1990.*
Suzuki et al., Journal of Bacteriology, vol. 170, No. 6, pp. 2886-2889, 1988.*
Sigma Chemical Company 1990 Catalog [Published by the Sigma Chemical Company, P.O. Box 14508, St. Louis, Missouri 63178] pp. 776-778, 1990.*
Brewer, et al., "Mechanistic Independence of Avian Myeloblastosis Virus DNA Polymerase and Ribonuclease H," Dec. 1974, J. Virol., 14(6):1494-1502, ASM, USA.

(Continued)

*Primary Examiner*—Ardin H. Marschel
(74) *Attorney, Agent, or Firm*—Charles B. Cappellari

(57) ABSTRACT

A method, composition and kit for synthesizing multiple copies of a target nucleic acid sequence autocatalytically under conditions of substantially constant temperature, ionic strength, and pH are provided in which multiple RNA copies of the target sequence autocatalytically generate additional copies using a mixture of blocked and unblocked primers and/or promoter-primers to initiate DNA and RNA synthesis, preferably with reduced non-specific product formation. The invention is useful for generating copies of a nucleic acid target sequence for purposes that include assays to quantitate specific nucleic acid sequences in clinical, environmental, forensic and similar samples, cloning and generating probes.

156 Claims, 1 Drawing Sheet

OTHER PUBLICATIONS

Champoux, et al., "Mechanism of RNA Primer Removal by the RNase H Activity of Avian Myeloblastosis Virus Reverse Transcriptase," Mar. 1984, J. Virol., 49(3):686-691, ASM, USA.

Collett, et al., "In Vitro Transcription of 70S RNA by the RNA-Directed DNA Polymerase of Rouse Sarcoma Virus: Lack of Influence by RNAse H," Jan. 1976, J. Virol. 17(1):291-5, PMID: 54443, ASM, USA.

Crouch, R.J., "Ribonuclease H: from discovery to 3D structure," Sep. 1990, New Biol., 2(9):771-7, PMID: 2177653.

Day, R., "How to Write and Publish a Scientific Paper," 2nd Ed., Philadelphia: ISI Press, 1983, p. 170.

Fahy, et al., "Self-sustained sequence replication (3SR): an isothermal transcription-based amplification system alternative to PCR," Aug. 1991, PCR Methods Appl., 1(1):25-33, PMID: 1842917.

Grandgenett, et al., "Different Mode of Action of Ribonuclease H in Purified alpha and alpha beta Ribonucleic Acid-Directed Deoxyribonucleic Acid Polymerase from Avian Myeloblastosis Virus" Aug. 25, 1974, J. Biol. Chem., 249(16):5148-5152, USA.

Kacian, et. al., "Synthesis of extensive, possibly complete, DNA copies of poliovirus RNA in high yields and at high specific activities," Jul. 1976, Proc. Natl. Acad. Sci., 73(7): 2191-2195, USA.

Kacian, et al., "Anticomplementary nature of smaller DNA produced during synthesis of extensive DNA copies of poliovirus RNA," Oct. 1976, Proc. Natl. Acad. Sci., 73(10): 3408-3412, USA.

Keller, et al., "Degradation of DNA RNA Hybrids by Ribonuclease H and DNA Polymerase of Cellular and Viral Origin," Nov. 1972, Proc. Natl. Acad. Sci. 69(11):3360-3364, USA.

Maniatis, et al., Molecular Cloning, 1982, COld Spring Harbor, N.Y.: Cold Spring Harbor Press, pp. 128, 213-214.

Marcus, et al., "Reverse Transcriptase-Associated RNAse H Activity II. Inhibition by Natural and Synthetic RNA," Sep. 1978, J. Virol. 27(3):576-581, ASM, USA.

Modak, et al., "Specific Inhibition of DNA Polymerase-Associated RNAse H by DNA," Apr. 1977, J. Virol., 22(1): 243-246, ASM, USA.

Moelling, K., "Characterization of reverse transcriptase and RNase H from friend-murine leukemia virus," Nov. 1974, Virology, 62(1):46-59, PMID: 4138103.

Myers, et al., "RNA primer used in synthesis of anticomplementary DNA by reverse transcriptase of avian myeloblastosis virus," Mar. 1980, Proc. Natl. Acad. Sci., 77(3) 1316-1320, USA.

Myers, et al., "Sodium pyrophosphate inhibition of RNA-DNA hybrid degradation by reverse transcriptase," Nov. 1978, Proc. Natl. Acad. Sci., 75(11):5329-5333, USA.

Myers, et al., "Synthesis of full-length DNA copies of avian myeloblastosis virus RNA in high yields," Jul. 1977, Proc. Natl. Acad. Sci., 74(7):2840-2843, USA.

Resnick, et al., "Involvement of Retrovirus Reverse Transcriptase-Associated RNAse H in Initiation of Strong Stop (+) DNA Synthesis and the Generation of the Long Terminal Repeat," Sep. 1984, J. Virol. 51(3):813-821, ASM, USA.

Rogall, et al., "Differentiation of Mycobacterium species by direct sequencing of amplified DNA," Sep. 1990, J. Gen. Microbiol., 136(Pt. 9):1915-1920, PMID: 2283506.

Srivastava, et al., "Reverse transcriptase-associated RNase H. Part IV. Pyrophosphate does not inhibit RNase H activity of AMV DNA polymerase," Dec. 14, 1979, Biochem. Biophys. Res. Commun., 91(3):892-899, PMID: 93479.

Wintersberger, U., "Ribonucleases H of retroviral and cellular origin," 1990, Pharmacol. Ther., 48(2):259-280 PMID: 1963496.

Wohrl, et al., "Mutations of a conserved residue within HIV-1 ribonuclease H affect its exo-and endonuclease activities," Aug. 5, 1991, J. Mol. Biol., 220(3):801-818, PMID: 1714505.

*Bethesda Resarch Laboratories Catalogue and Reference Guide,* Bethesda Research Laboratories, Bethesda, MD (1988) p. 37.

Both et al., "A general strategy for cloning double-stranded RNA: nucleotide sequence of the Simian-11 rotavirus gene 8," *Nucleic Acids Research* 10:7075 (1982).

Cashdollar et al., "Cloning the Double-stranded RNA Genes of a Reovirus: Sequence of the cloned S2 gene," *Proc. Natl. Acad. Sci. USA* 79:7644-7648 (1982).

Cox et al., "The 16S ribosomal RNA of *Mycobacterium leprae* contains a unique equence which can be used for identification by the polymerase chain reaction," *J. Med. Microbiol.,* 35:284-290 (1991).

Golomb and Grandgenett, "Endonuclease Activity of Purified RNA-directed DNA Polymerase from Avian Myeloblastosis Virus," *The Journal of Biological Chemistry* 254:1606-1613 (1979).

Grachev et al., "Oligonucleotides complementary to a promoter over the region -8 . . . +2 as transcription primers for *E. coli* RNA polymerase," *Nucleic Acids Research* 12:8509 (1984).

Guatelli et al., "Isothermal, in vitro amplification of nucleic acids by a multienzyme reaction modeled after retroviral replication," *Proc. Natl. Acad. Sci. USA* 87:1874-1878 (1990).

Gubler, *Guide to Molecular Cloning Techniques,* Academic Press, NY, NY (1987) p. 330.

Hayes, "The Genetics of Bacteria and their Viruses," John Wiley & Sons Inc., 2nd ed.:239-257, New York (1964).

Joyce, "Amplification, Mutation and Selection of Catalytic RNA," *Gene,* 82:83-87 (1989).

Khorana, "Total Synthesis of a Gene," *Science,* 203:614-25 (1979).

Krug and Berger, "Ribonuclease H activities associated with viral reverse transcriptases are endocucleases," *Proc. Natl. Acad. Sci. USA* 86:3539-3543 (1989).

Krug & Berger, "First-Strand cDNA Synthesis Primed with Oligo(dT)," (Methods in Enzymology) *Guide to Molecular Cloning Techniques,* Berger and Kimmel, eds., (Academic Press:NY, 1987) vol. 152, pp. 316-325.

Kupper et al., "Promoter-dependent transciption of TRNA$^{tyr}$ genes using DNA fragments produced by restriction enzymes," *Proc. Natl. Acad. Sci. USA* 72:4754 (1975).

Kwoh et al., "Transcription-based amplification system and detection of amplified human immunodeficiency virus type 1 with a bead-based sandwich hybridization format," *Proc. Natl. Acad. Sci. USA* 86:1173-1177 (1989).

Leis et al., "Mechanism of Action of the Endonuclease Associated with the αβ and ββ Forms of Avian RNA Tumor Virus Reverse Transcriptase," *Journal of Virology* 45:727-739 (1983).

Lomonossoff, et al., "The Location of the First AUG Condons in Cowpea Mosaic Virus RNAs," *Nucleic Acids Research,* 10,16:4861-72 (1982).

Lowary et al., "A Better Way to Make RNA for Physical Studies," Structure & Dynamics of RNA, Nato AS1 Series Knippenberg, eds. (New York: Plenum Press, 1986) vol. 110.

Milligan et al., "Oligoribonucleotide synthesis using T7 RNA polymerase and synthetic DNA templates," *Nucleic Acids Research* 15:8783-98 (1987).

Mullis and Faloona, "Specific Synthesis of DNA in Vitro via a Polymerase-Catalyzed Chain Reaction," *Methods in Enzymology,* 155:355-349 (1987).

Murakawa et al., "Direct Detection of HIV-1 RNA from AIDS and ARC Patient Samples," *DNA,* 7:287-295, 1988.

Okayama and Berg, "High-Efficiency Cloning of Full-Length cDNA," *Molecular and Cellular Biology* 2:161-170, 1982.

Oyama et al., "Intrinsic Properties of Reverse Transcriptase in Reverse Transcription," *J. Biol. Chem.* 264:18808-18817 (1989).

Rossi et al., "An Alternate Method for Synthesis of Double-stranded DNA segments," *J. Biol. Chem.* 257:9226 (1982).

Stent, "Molecular Biology of Bacterial Viruses," W.H. Freeman & Company, 157-63, San Francisco (1963).

Tyagi et al., *Trop. Med. Parasitol.* 41:294-296 (1990).

Watson and Crick, "Molecular Structure of Nucleic Acids," *Nature,* Apr. 25, 1953, p. 737.

Watson & Crick, "Genetical Implications of the Structure of Deoxyribonucleic Acid," *Nature,* 171:964-967 (1953).

Wilk et al., "Backbone-modified oligonucleotides containing a butaneodiol-1,3 moiety as a 'vicarious segment' for the deoxyribosyl moiety—synthesis and enzyme studies," *Nucleic Acids Research* 18:2065-2068 (1990).

Zoller and Smith, "Oligonucleotide-Directed Mutagenesis of DNA Fragments Cloned into M13 Vectors," *Methods in Enzymology,* 100:468-500 (1983).

Stahl et al., "The Division between Fast- and Slow-Growing Species Corresponds to Natural Relationships among the Mycobacteria," J.Bactertology, Jan. 1990, 172(1):116-124, Am. Soc. for Microbiology, Washington, DC, USA.

* cited by examiner

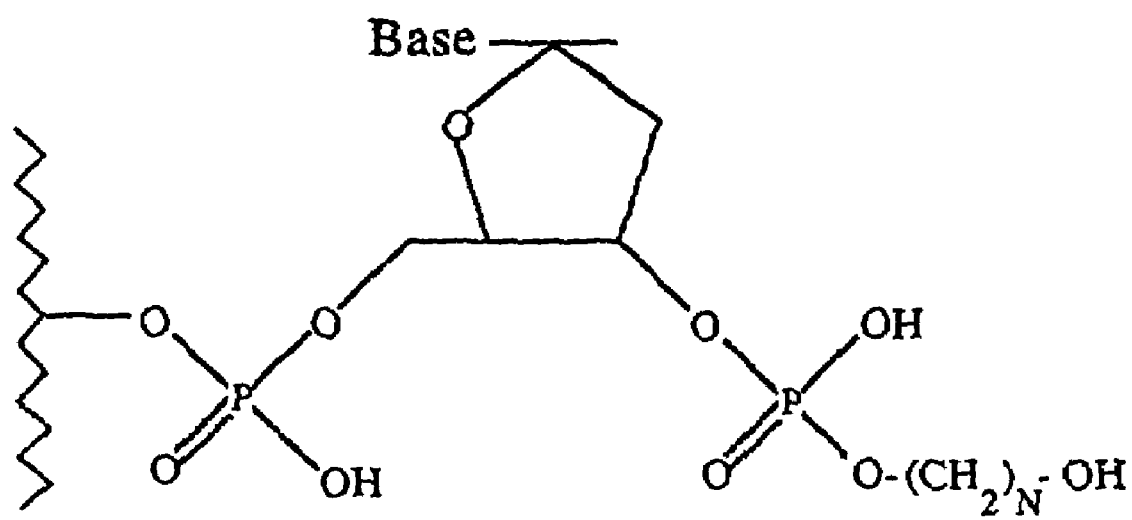
3' alkane diol modified nucleotide. When N = 3, the modification is referred to as RP.

SEQUENCE LISTING

<160> NUMBER OF SEQ ID NOS: 46

<210> SEQ ID NO 1
<211> LENGTH: 428
<212> TYPE: DNA
<213> ORGANISM: Trichoderma reesei
<220> FEATURE:
<221> NAME/KEY: intron
<222> LOCATION: (167)..(236)
<220> FEATURE:
<221> NAME/KEY: intron
<222> LOCATION: (323)..(386)
<220> FEATURE:
<221> NAME/KEY: misc_feature
<223> OTHER INFORMATION: Coding sequence of hfb1

<400> SEQUENCE: 1

```
atgaagttct tcgccatcgc cgctctcttt gccgccgctg ccgttgccca gcctctcgag      60
gaccgcagca acggcaacgg caatgtttgc cctcccggcc tcttcagcaa cccccagtgc     120
tgtgccaccc aagtccttgg cctcatcggc cttgactgca aagtccgtaa gttgagccat     180
aacataagaa tcctcttgac ggaaatatgc cttctcactc ctttacccct gaacagcctc     240
ccagaacgtt tacgacggca ccgacttccg caacgtctgc gccaaaaccg gcgcccagcc     300
tctctgctgc gtggcccccg ttgtaagttg atgcccagc tcaagctcca gtctttggca     360
aacccattct gacacccaga ctgcaggccg gccaggctct tctgtgccag accgccgtcg     420
gtgcttga                                                              428
```

<210> SEQ ID NO 2
<211> LENGTH: 78
<212> TYPE: DNA
<213> ORGANISM: Artificial Sequence
<220> FEATURE:
<223> OTHER INFORMATION: Description of Artificial Sequence: PCR 5'
      primer

<400> SEQUENCE: 2

```
tcgggcacta cgtgccagta tagcaacgac tactactcgc aatgccttgt tccgcgtggc      60
tctagttctg gaaccgca                                                    78
```

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: PCR 3'
      primer

<400> SEQUENCE: 3

```
tcgtacggat cctcaagcac cgacggcggt                                       30
```

<210> SEQ ID NO 4
<211> LENGTH: 63
<212> TYPE: DNA
<213> ORGANISM: Artificial Sequence
<220> FEATURE:
<223> OTHER INFORMATION: Description of Artificial Sequence: PCR 5'
      primer

<400> SEQUENCE: 4

```
actacacgga ggagctcgac gacttcgagc agcccgagct gcacgcagag caacggcaac      60
ggc                                                                    63
```

<210> SEQ ID NO 5
<211> LENGTH: 2211
<212> TYPE: DNA
<213> ORGANISM: Trichoderma reesei
<220> FEATURE:
<221> NAME/KEY: promoter
<222> LOCATION: (1)..(2211)
<223> OTHER INFORMATION: cbh1 promoter sequence

<400> SEQUENCE: 5

```
gaattctcac ggtgaatgta ggccttttgt agggtaggaa ttgtcactca agcaccccca      60
acctccatta cgcctccccc atagagttcc caatcagtga gtcatggcac tgttctcaaa     120
tagattgggg agaagttgac ttccgcccag agctgaaggt cgcacaaccg catgatatag     180
ggtcggcaac ggcaaaaaag cacgtggctc accgaaaagc aagatgtttg cgatctaaca     240
tccaggaacc tggatacatc catcatcacg cacgaccact ttgatctgct ggtaaactcg     300
tattcgccct aaaccgaagt gcgtggtaaa tctacacgtg ggcccctttc ggtatactgc     360
gtgtgtcttc tctaggtgca ttcttttcctt cctctagtgt tgaattgttt gtgttgggag     420
tccgagctgt aactacctct gaatctctgg agaatggtgg actaacgact accgtgcacc     480
tgcatcatgt atataatagt gatcctgaga agggggggttt ggagcaatgt gggactttga     540
tggtcatcaa acaaagaacg aagacgcctc ttttgcaaag ttttgtttcg ctacggtga     600
agaactggat acttgttgtg tcttctgtgt attttttgtgg caacaagagg ccagagacaa     660
tctattcaaa caccaagctt gctcttttga gctacaagaa cctgtggggt atatatctag     720
agttgtgaag tcggtaatcc cgctgtatag taatacgagt cgcatctaaa tactccgaag     780
ctgctgcgaa cccggagaat cgagatgtgc tggaaagctt ctagcgagcg gctaaattag     840
catgaaaggc tatgagaaat tctggagacg gcttgttgaa tcatggcgtt ccattcttcg     900
acaagcaaag cgttccgtcg cagtagcagg cactcattcc cgaaaaaact cggagattcc     960
taagtagcga tggaaccgga ataatataat aggcaataca ttgagttgcc tcgacggttg    1020
caatgcaggg gtactgagct tggacataac tgttccgtac cccacctctt ctcaaccttt    1080
ggcgtttccc tgattcagcg tacccgtaca agtcgtaatc actattaacc cagactgacc    1140
ggacgtgttt tgcccttcat ttggagaaat aatgtcattg cgatgtgtaa tttgcctgct    1200
tgaccgactg gggctgttcg aagcccgaat gtaggattgt tatccgaact ctgctcgtag    1260
aggcatgttg tgaatctgtg tcgggcagga cacgcctcga aggttcacgg caagggaaac    1320
caccgatagc agtgtctagt agcaacctgt aaagccgcaa tgcagcatca ctggaaaata    1380
caaaccaatg gctaaaagta cataagttaa tgcctaaaga agtcatatac cagcggctaa    1440
taattgtaca atcaagtggc taaacgtacc gtaatttgcc aacgcgttgt ggggttgcag    1500
aagcaacggc aaagcccact tcccacgttt gtttcttcac tcagtccaat ctcagctggt    1560
gatcccccaa ttgggtcgct tgtttgttcc ggtgaagtga agaagacag aggtaagaat    1620
gtctgactcg gagcgttttg catacaacca agggcagtga tggaagacag tgaaatgttg    1680
acattcaagg agtatttagc cagggatgct tgagtgtatc gtgtaaggag gtttgtctgc    1740
cgatacgacg aatactgtat agtcacttct gatgaagtgg tccatattga aatgtaagtc    1800
ggcactgaac aggcaaaaga ttgagttgaa actgcctaag atctcgggcc ctcgggcttc    1860
ggctttgggt gtacatgttt gtgctccggg caaatgcaaa gtgtggtagg atcgacacac    1920
tgctgccttt accaagcagc tgagggtatg tgataggcaa atgttcaggg gccactgcat    1980
```

| | |
|---|---|
| ggtttcgaat agaaagagaa gcttagccaa gaacaatagc cgataaagat agcctcatta | 2040 |
| aacgaaatga gctagtaggc aaagtcagcg aatgtgtata tataaaggtt cgaggtccgt | 2100 |
| gcctccctca tgctctcccc atctactcat caactcagat cctccaggag acttgtacac | 2160 |
| catcttttga ggcacagaaa cccaatagtc aaccgcggac tgcgcatcat g | 2211 |

<210> SEQ ID NO 6
<211> LENGTH: 1588
<212> TYPE: DNA
<213> ORGANISM: Trichoderma reesei
<220> FEATURE:
<221> NAME/KEY: misc_feature
<223> OTHER INFORMATION: T. reesei egl1 cDNA

<400> SEQUENCE: 6

| | |
|---|---|
| cccccctatc ttagtccttc ttgttgtccc aaaatggcgc cctcagttac actgccgttg | 60 |
| accacggcca tcctggccat tgcccggctc gtcgccgccc agcaaccggg taccagcacc | 120 |
| cccgaggtcc atcccaagtt gacaacctac aagtgtacaa agtccggggg gtgcgtggcc | 180 |
| caggacacct cggtggtcct tgactggaac taccgctgga tgcacgacgc aaactacaac | 240 |
| tcgtgcaccg tcaacggcgg cgtcaacacc acgctctgcc ctgacgaggc gacctgtggc | 300 |
| aagaactgct tcatcgaggg cgtcgactac gccgcctcgg gcgtcacgac ctcgggcagc | 360 |
| agcctcacca tgaaccagta catgcccagc agctctggcg gctacagcag cgtctctcct | 420 |
| cggctgtatc tcctggactc tgacggtgag tacgtgatgc tgaagctcaa cggccaggag | 480 |
| ctgagcttcg acgtcgacct ctctgctctg ccgtgtggag agaacggctc gctctacctg | 540 |
| tctcagatgg acgagaacgg gggcgccaac cagtataaca cggccggtgc caactacggg | 600 |
| agcggctact gcgatgctca gtgccccgtc agacatgga ggaacggcac cctcaacact | 660 |
| agccaccagg gcttctgctg caacgagatg gatatcctgg agggcaactc gagggcgaat | 720 |
| gccttgaccc ctcactcttg cacggccacg gcctgcgact ctgccggttg cggcttcaac | 780 |
| ccctatggca gcggctacaa aagctactac ggccccggag ataccgttga cacctccaag | 840 |
| accttcacca tcatcaccca gttcaacacg gacaacggct cgccctcggg caaccttgtg | 900 |
| agcatcaccc gcaagtacca gcaaaacggc gtcgacatcc ccagcgccca gcccggcggc | 960 |
| gacaccatct cgtcctgccc gtccgcctca gcctacggcg gcctcgccac catgggcaag | 1020 |
| gccctgagca gcggcatggt gctcgtgttc agcatttgga acgacaacag ccagtacatg | 1080 |
| aactggctcg acagcggcaa cgccggcccc tgcagcagca ccgagggcaa cccatccaac | 1140 |
| atcctggcca caaccccaa cacgcacgtc gtcttctcca acatccgctg gggagacatt | 1200 |
| gggtctacta cgaactcgac tgcgcccccg ccccgcctg cgtccagcac gacgttttcg | 1260 |
| actacacgga ggagctcgac gacttcgagc agcccgagct gcacgcagac tcactggggg | 1320 |
| cagtgcggtg gcattgggta cagcgggtgc aagacgtgca cgtcgggcac tacgtgccag | 1380 |
| tatagcaacg actactactc gcaatgcctt tagagcgttg acttgcctct ggtctgtcca | 1440 |
| gacggggca cgatagaatg cgggcacgca gggagctcgt agacattggg cttaatatat | 1500 |
| aagacatgct atgttgtatc tacattagca aatgacaaac aaatgaaaaa gaacttatca | 1560 |
| agcaaaaaaa aaaaaaaaaa aaaaaaaa | 1588 |

<210> SEQ ID NO 7
<211> LENGTH: 745
<212> TYPE: DNA
<213> ORGANISM: Trichoderma reesei
<220> FEATURE:

<221> NAME/KEY: terminator
<222> LOCATION: (1)..(745)
<223> OTHER INFORMATION: T. reesei cbh1 terminator

<400> SEQUENCE: 7

| | |
|---|---|
| ggacctaccc agtctcacta cggccagtgc ggcggtattg gctacagcgg ccccacggtc | 60 |
| tgcgccagcg gcacaacttg ccaggtcctg aacccttact actctcagtg cctgtaaagc | 120 |
| tccgtgcgaa agcctgacgc accggtagat tcttggtgag cccgtatcat gacggcggcg | 180 |
| ggagctacat ggccccgggt gatttatttt ttttgtatct acttctgacc cttttcaaat | 240 |
| atacggtcaa ctcatctttc actggagatg cggcctgctt ggtattgcga tgttgtcagc | 300 |
| ttggcaaatt gtggctttcg aaaacacaaa acgattcctt agtagccatg catttttaaga | 360 |
| taacggaata gaagaaagag gaaattaaaa aaaaaaaaa aacaaacatc ccgttcataa | 420 |
| cccgtagaat cgccgctctt cgtgtatccc agtaccacgt caaaggtatt catgatcgtt | 480 |
| caatgttgat attgttccgc cagtatggct ccaccccat ctccgcgaat ctcctcttct | 540 |
| cgaacgcggt agtggctgct gccaattggt aatgaccata gggagacaaa cagcataata | 600 |
| gcaacagtgg aaattagtgg cgcaataatt gagaacacag tgagaccata gctggcggcc | 660 |
| tggaaagcac tgttggagac caacttgtcc gttgcgaggc caacttgcat tgctgtcaag | 720 |
| acgatgacaa cgtagccgag gaccc | 745 |

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: annealed primer

<400> SEQUENCE: 8

| | |
|---|---|
| taaccgcggt | 10 |

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: annealed primer

<400> SEQUENCE: 9

| | |
|---|---|
| ctagaccgcg gttaat | 16 |

<210> SEQ ID NO 10
<211> LENGTH: 1232
<212> TYPE: DNA
<213> ORGANISM: Trichoderma reesei
<220> FEATURE:
<221> NAME/KEY: promoter
<222> LOCATION: (1)..(1232)
<223> OTHER INFORMATION: T. reesei gpd1 promotor

<400> SEQUENCE: 10

| | |
|---|---|
| gtcgacacga tatacaggcg cggctgatga taatgatgat cgagcatgac ttgatgctgt | 60 |
| atgtgacaat attgactgcg aggaaccatc aggtgtgtat ggatggaatc attctgtaac | 120 |
| caccaaggtg catgcatcat aaggattctc ctcagctcac caacaacgaa cgatggccat | 180 |
| gttagtgaag gcaccgtgat ggcaagatag aaccactatt gcatctgcgc ttcccacgca | 240 |
| cagtacgtca agtaacgtca aagccgccct cccgtaacct cgcccgttgt tgctcccccc | 300 |

-continued

```
gattgcctca atcacatagt acctacctat gcattatggg cggcctcaac ccaccccccc      360
agattgagag ctaccttaca tcaatatggc cagcacctct tcggcgatac atactcgcca      420
ccccagccgg cgcgattgtg tgtactaggt aggctcgtac tataccagca ggagaggtgc      480
tgcttggcaa tcgtgctcag ctgttaggtt gtacttgtat ggtacttgta aggtggtcat      540
gcagttgcta aggtacctag ggagggattc aacgagccct gcttccaatg tccatctgga      600
taggatggcg gctggcgggg ccgaagctgg gaactcgcca acagtcatat gtaatagctc      660
aagttgatga taccgttttg ccagattaga tgcgagaagc agcatgaatg tcgctcatcc      720
gatgccgcat caccgttgtg tcagaaacga ccaagctaag caactaaggt accttaccgt      780
ccactatctc aggtaaccag gtactaccag ctaccctacc tgccgtgcct acctgcttta      840
gtgttaatct ttccacctcc ctcctcaatc ttctttttccc tcctctcctc tttttttttt      900
cttcctcctc ttcttctcca taaccattcc taacaacatc gacattctct cctaatcacc      960
agcctcgcaa atcctcagtt tgtatgtacg tacgtactac aatcatcacc acgatcgtcc     1020
gcccgacgat gcggcttctg ttcgcctgcc cctcctctca ctcgtgccct tgacgagcta     1080
gccccgccag gactctcctg cgtcaccaat ttttttccct atttacccct cctccctctc     1140
tccctctcgt ttcttcctaa caaacaacca ccaccaaaat ctctttggaa gctcacgact     1200
cacgcagctc aattcgcaga tacaaatcta ga                                   1232
```

<210> SEQ ID NO 11
<211> LENGTH: 1129
<212> TYPE: DNA
<213> ORGANISM: Trichoderma reesei
<220> FEATURE:
<221> NAME/KEY: terminator
<222> LOCATION: (1)..(1129)
<223> OTHER INFORMATION: T. reesei gpd1 terminator

<400> SEQUENCE: 11

```
ggatcccgag cattgtctat gaatgcaaac aaaaatagta aataaatagt aattctggcc       60
atgacgaata gagccaatct gctccacttg actatcttgt gactgtatcg tatgtcgaac      120
ccttgactgc ccattcaaac aattgtaaag gaatatagct acaagttatg tctcacgttt      180
gcgtgcgagc ccgtttgtac gttatttttga gaaagcgttg ccatcacatg ctcacagtca      240
cttggcttac gatcatgttt gcgatcttcg gtaagaatac acagagtaac gattatctcc      300
atcgcttcta tgattaggta ctcagacaac acatgggaaa caagataacc atcgcatgca      360
aggtcgattc caatcatgat ctggactggg gtattccatc taagccatag taccctcgag      420
agaaggaatg gtaggacctc tcaggcgtcc accatctgtg ctgcaaatcc aagaaacccc      480
ccaaaagcac ctacctatct acctagagta actgcacgag aaaagaaaag gagcagaaga      540
agaatgatct caagaggccg tgaacgcaga aacacactcc tcccaacttt tcaagttttg      600
aacaaaaaaa gaaagatgag gactagaaga tggagtattt ccttcttaga gagctctcgg      660
tgaggtgacc tgtcagggtt taccgcaaac cgtcggtggt tctatccaat taatcaagtc      720
ccgcgcctcg cctcttctct cctgtccttt catagaatcc cgtctccttg ttgcttgatc      780
gaagcggggt tatcgacgcc accaaagatc ttgtcttggt gacttatcaa tccttttggtg      840 atcaaacagc ccccgagtga tcagatccgt aaaagaagaa gaagagtacg atttaaccag      900
accgaggaac aataaagcga gtaaataaca tcaaaataag agtctcgttg aaaattactt      960
gttcctcaat caatcccaac cccctaaaa gcccttcccc ccatggtata tcccggcagt     1020
```

-continued aggagagaga tatttccact accgctcacc accaagtgag gcttgccgag agaagaggat    1080
gaatcagaag tgacaacaac gggttgagca catgggatat cggcgcgcc               1129

<210> SEQ ID NO 12
<211> LENGTH: 5733
<212> TYPE: DNA
<213> ORGANISM: Aspergillus nidulans
<220> FEATURE:
<221> NAME/KEY: misc_feature
<223> OTHER INFORMATION: (1-5733) Sequence of plasmid pAN52-1
<220> FEATURE:
<221> NAME/KEY: promoter
<222> LOCATION: (1)..(2129)
<223> OTHER INFORMATION: A. nidulans gpdA promoter
<220> FEATURE:
<221> NAME/KEY: gene
<222> LOCATION: (2130)..(2304)
<223> OTHER INFORMATION: A. nidulans gpdA gene
<220> FEATURE:
<221> NAME/KEY: terminator
<222> LOCATION: (2305)..(3071)
<223> OTHER INFORMATION: A. nidulans trpC terminator
<220> FEATURE:
<221> NAME/KEY: misc_feature
<222> LOCATION: (3072)..(5726)
<223> OTHER INFORMATION: pUC18 from SalI to EcoRI

<400> SEQUENCE: 12 caattcccctt gtatctctac acacaggctc aaatcaataa gaagaacggt tcgtcttttt    60
cgtttatatc ttgcatcgtc ccaaagctat tggcgggata ttctgtttgc agttggctga   120
cttgaagtaa tctctgcaga tctttcgaca ctgaaatacg tcgagcctgc tccgcttgga   180
agcggcgagg agcctcgtcc tgtcacaact accaacatgg agtacgataa gggccagttc   240
cgccagctca ttaagagcca gttcatgggc gttggcatga tggccgtcat gcatctgtac   300
ttcaagtaca ccaacgctct tctgatccag tcgatcatcc gctgaaggcg ctttcgaatc   360
tggttaagat ccacgtcttc gggaagccag cgactggtga cctccagcgt ccctttaagg   420
ctgccaacag ctttctcagc cagggccagc caagaccga caaggcctcc ctccagaacg   480
ccgagaagaa ctggagggt ggtgtcaagg aggagtaagc tccttattga agtcggagga   540
cggagcggtg tcaagaggat attcttcgac tctgtattat agataagatg atgaggaatt   600
ggaggtagca tagcttccatt tggatttgct ttccaggctg agactctagc ttggagcata   660
gagggtcctt tggctttcaa tattctcaag tatctcgagt ttgaacttat tccctgtgaa   720 cctttttattc accaatgagc attggaatga acatgaatct gaggactgca atcgccatga   780
ggttttcgaa atacatccgg atgtcgaagg cttgggcac ctgcgttggt tgaatttaga   840
acgtggcact attgatcatc cgatagctct gcaaagggcg ttgcacaatg caagtcaaac   900
gttgctagca gttccaggtg gaatgttatg atgagcattg tattaaatca ggagatatag   960
catgatctct agttagctca ccacaaaagt cagacggcgt aaccaaaagt cacacaacac  1020
aagctgtaag gatttcggca cggctacgga agacggagaa gccaccttca gtggactcga  1080 gtaccatttta attctatttg tgtttgatcg agacctaata cagcccctac aacgaccatc  1140
aaagtcgtat agctaccagt gaggaagtgg actcaaatcg acttcagcaa catctcctgg  1200
ataaacttta agcctaaact atacagaata agataggtgg agagcttata ccagctcccc  1260
aaatctgtcc agatcatggt tgaccggtgc ctggatcttc ctatagaatc atccttattc  1320
gttgacctag ctgattctgg agtgacccaa agggtcatga cttgagccta aaatccgccg  1380
cctccaccat ttgtagaaaa atgtgacgaa ctcgtgagct ctgtacagtg accggtgact  1440

```
ctttctggca tgcggagaga cggacggacg cagagagaag ggctgagtaa taagccactg    1500
gccagacagc tctggcggct ctgaggtgca gtggatgatt attaatccgg gaccggccgc    1560
ccctccgccc cgaagtggaa aggctggtgt gcccctcgtt gaccaagaat ctattgcatc    1620
atcggagaat atggagcttc atcgaatcac cggcagtaag cgaaggagaa tgtgaagcca    1680
ggggtgtata gccgtcggcg aaatagcatg ccattaacct aggtacagaa gtccaattgc    1740
ttccgatctg gtaaaagatt cacgagatag taccttctcc gaagtaggta gagcgagtac    1800
ccggcgcgta agctccctaa ttggcccatc cggcatctgt agggcgtcca aatatcgtgc    1860
ctctcctgct ttgcccggtg tatgaaaccg gaaaggccgc tcaggagctg ccagcggcg    1920 cagaccggga acacaagctg gcagtcgacc catccggtgc tctgcactcg acctgctgag    1980
gtccctcagt ccctggtagg cagctttgcc ccgtctgtcc gcccggtgtg tcggcggggt    2040
tgacaaggtc gttgcgtcag tccaacattt gttgccatat tttcctgctc tccccaccag    2100
ctgctctttt cttttctctt tcttttccca tcttcagtat attcatcttc ccatccaaga    2160 accttatt ccctaagta agtactttgc tacatccata ctccatcctt cccatccctt    2220
attcctttga acctttcagt tcgagctttc ccacttcatc gcagcttgac taacagctac    2280
cccgcttgag cagacatcac catggatcca cttaacgtta ctgaaatcat caaacagctt    2340
gacgaatctg gatataagat cgttggtgtc gatgtcagct ccggagttga dacaaatggt    2400
gttcaggatc tcgataagat acgttcattt gtccaagcag caaagagtgc cttctagtga    2460
tttaatagct ccatgtcaac aagaataaaa cgcgttttcg ggtttacctc ttccagatac    2520
agctcatctg caatgcatta atgcattgac tgcaacctag taacgccttn caggctccgg    2580
cgaagagaag aatagcttag cagagctatt ttcatttcg ggagacgaga tcaagcagat    2640
caacggtcgt caagagacct acgagactga ggaatccgct cttggctcca cgcgactata    2700
tatttgtctc taattgtact ttgacatgct cctcttcttt actctgatag cttgactatg    2760
aaaattccgt caccagcncc tgggttcgca agataattg catgtttctt ccttgaactc    2820
tcaagcctac aggacacaca ttcatcgtag gtataaacct cgaaatcant tcctactaag    2880
atggtataca atagtaacca tgcatggttg cctagtgaat gctccgtaac acccaatacg    2940
ccggccgaaa cttttttaca actctcctat gagtcgttta cccagaatgc acaggtacac    3000
ttgtttagag gtaatccttc tttctagaag tcctcgtgta ctgtgtaagc gcccactcca    3060
catctccact cgacctgcag gcatgcaagc ttggcactgg ccgtcgtttt acaacgtcgt    3120
gactgggaaa accctggcgt tacccaactt aatcgccttg cagcacatcc ccctttcgcc    3180
agctggcgta atagcgaaga ggcccgcacc gatcgccctt ccaacagttg cgcagcctg    3240 aatggcgaat ggcgcctgat gcggtatttt ctccttacgc atctgtgcgg tatttcacac    3300
cgcatatggt gcactctcag tacaatctgc tctgatgccg catagttaag ccagccccga    3360
cacccgccaa cacccgctga cgcgcccctga cgggcttgtc tgctcccggc atccgcttac    3420
agacaagctg tgaccgtctc cgggagctgc atgtgtcaga ggttttcacc gtcatcaccg    3480
aaacgcgcga cgcaaaggg cctcgtgata cgcctatttt tataggttaa tgtcatgata    3540
ataatggttt cttagacgtc aggtggcact tttcggggaa atgtgcgcgg aacccctatt    3600
tgtttatttt tctaaataca ttcaaatatg tatccgctca tgagacaata accctgataa    3660
atgcttcaat aatattgaaa aaggaagagt atgagtattc aacatttccg tgtcgccctt    3720 attcccttt ttgcggcatt ttgccttcct gtttttgctc acccagaaac gctggtgaaa    3780
gtaaaagatg ctgaagatca gttgggtgca cgagtgggtt acatcgaact ggatctcaac    3840
```

```
agcggtaaga tccttgagag ttttcgcccc gaagaacgtt ttccaatgat gagcactttt    3900
aaagttctgc tatgtggcgc ggtattatcc cgtattgacg ccgggcaaga gcaactcggt    3960
cgccgcatac actattctca gaatgacttg gttgagtact caccagtcac agaaaagcat    4020
cttacggatg gcatgacagt aagagaatta tgcagtgctg ccataaccat gagtgataac    4080
actgcggcca acttacttct gacaacgatc ggaggaccga aggagctaac cgcttttttg    4140
cacaacatgg gggatcatgt aactcgcctt gatcgttggg aaccggagct gaatgaagcc    4200
ataccaaacg acgagcgtga caccacgatg cctgtagcaa tggcaacaac gttgcgcaaa    4260
ctattaactg gcgaactact tactctagct tcccggcaac aattaataga ctggatggag    4320
gcggataaag ttgcaggacc acttctgcgc tcggcccttc cggctggctg gtttattgct    4380
gataaatctg gagccggtga gcgtgggtct cgcggtatca ttgcagcact ggggccagat    4440
ggtaagccct cccgtatcgt agttatctac acgacgggga gtcaggcaac tatggatgaa    4500
cgaaatagac agatcgctga gataggtgcc tcactgatta agcattggta actgtcagac    4560
caagtttact catatatact ttagattgat ttaaaacttc atttttaatt taaaaggatc    4620
taggtgaaga tcctttttga taatctcatg accaaaatcc cttaacgtga gttttcgttc    4680
cactgagcgt cagaccccgt agaaaagatc aaaggatctt cttgagatcc ttttttctg    4740 cgcgtaatct gctgcttgca acaaaaaaa ccaccgctac cagcggtggt ttgtttgccg    4800
gatcaagagc taccaactct ttttccgaag gtaactggct tcagcagagc gcagatacca    4860
aatactgtcc ttctagtgta gccgtagtta ggccaccact tcaagaactc tgtagcaccg    4920
cctacatacc tcgctctgct aatcctgtta ccagtggctg ctgccagtgg cgataagtcg    4980
tgtcttaccg ggttggactc aagacgatag ttaccggata aggcgcagcg gtcgggctga    5040
acggggggtt cgtgcacaca gcccagcttg gagcgaacga cctacaccga actgagatac    5100
ctacagcgtg agctatgaga aagcgccacg cttcccgaag ggagaaaggc ggacaggtat    5160
ccggtaagcg gcagggtcgg aacaggagag cgcacgaggg agcttccagg gggaaacgcc    5220
tggtatcttt atagtcctgt cgggtttcgc cacctctgac ttgagcgtcg atttttgtga    5280
tgctcgtcag gggggcggag cctatggaaa aacgccagca acgcggcctt tttacggttc    5340
ctggcctttt gctggccttt tgctcacatg ttctttcctg cgttatcccc tgattctgtg    5400
gataaccgta ttaccgcctt tgagtgagct gataccgctc gccgcagccg aacgaccgag    5460
cgcagcgagt cagtgagcga ggaagcggaa gagcgcccaa tacgcaaacc gcctctcccc    5520
gcgcgttggc cgattcatta atgcagctgg cacgacaggt ttcccgactg gaaagcgggc    5580
agtgagcgca acgcaattaa tgtgagttag ctcactcatt aggcacccca ggctttacac    5640
tttatgcttc cggctcgtat gttgtgtgga attgtgagcg gataacaatt tcacacagga    5700
aacagctatg accatgatta cgaattgcgg ccg                                 5733
```

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: PCR 5'
      primer

<400> SEQUENCE: 13
gtcaaccgcg gactgcgcat catgaagttc ttcgccatc                           39

<210> SEQ ID NO 14
<211> LENGTH: 66
<212> TYPE: DNA
<213> ORGANISM: Artificial Sequence
<220> FEATURE:
<223> OTHER INFORMATION: Description of Artificial Sequence: PCR 5'
      primer

<400> SEQUENCE: 14
tctagcaagc ttggctctag ttctggaacc gcaccaggcg gcagcaacgg caacggcaat    60
gtttgc                                                               66

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: PCR 3'
      primer

<400> SEQUENCE: 15
tcgtacaagc tttcaagcac cgacggcggt                                     30

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: PCR 5'
      primer

<400> SEQUENCE: 16
tctagctcta gaagcaacgg caacggcaat gtt                                 33

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: PCR 3'
      primer

<400> SEQUENCE: 17
tgctagtcga cctgctagca gcaccgacgg cggtctg                             37

<210> SEQ ID NO 18
<211> LENGTH: 4614
<212> TYPE: DNA
<213> ORGANISM: Saccharomyces cerevisiae
<220> FEATURE:
<223> OTHER INFORMATION: S. cerevisiae FLO1 coding sequence

<400> SEQUENCE: 18
atgacaatgc ctcatcgcta tatgttttg gcagtctta cacttctggc actaactagt     60
gtggcctcag gagccacaga ggcgtgctta ccagcaggcc agaggaaaag tgggatgaat   120
ataaattttt accagtattc attgaaagat tcctccacat attcgaatgc agcatatatg   180
gcttatggat atgcctcaaa aaccaaacta ggttctgtcg gaggacaaac tgatatctcg   240
attgattata atattcccctg tgttagttca tcaggcacat ttccttgtcc tcaagaagat    300
tcctatggaa actggggatg caaaggaatg ggtgcttgtt ctaatagtca aggaattgca   360
tactggagta ctgatttatt tggttttctat actaccccaa caaacgtaac cctagaaatg   420
acaggttatt ttttaccacc acagacgggt tcttacacat tcaagtttgc tacagttgac   480

-continued

| | |
|---|---|
| gactctgcaa ttctatcagt aggtggtgca accgcgttca actgttgtgc tcaacagcaa | 540 |
| ccgccgatca catcaacgaa ctttaccatt gacggtatca agccatgggg tggaagtttg | 600 |
| ccacctaata tcgaaggaac cgtctatatg tacgctggct actattatcc aatgaaggtt | 660 |
| gtttactcga acgctgtttc ttggggtaca cttccaatta gtgtgacact tccagatggt | 720 |
| accactgtaa gtgatgactt cgaagggtac gtctattcct ttgacgatga cctaagtcaa | 780 |
| tctaactgta ctgtccctga cccttcaaat tatgctgtca gtaccactac aactacaacg | 840 |
| gaaccatgga ccggtacttt cacttctaca tctactgaaa tgaccaccgt caccggtacc | 900 |
| aacggcgttc aactgacga aaccgtcatt gtcatcagaa ctccaacaac tgctagcacc | 960 |
| atcataacta caactgagcc atggaacagc acttttacct ctacttctac cgaattgacc | 1020 |
| acagtcactg gcaccaatgg tgtacgaact gacgaaacca tcattgtaat cagaacacca | 1080 |
| acaacagcca ctactgccat aactacaact gagccatgga acagcacttt tacctctact | 1140 |
| tctaccgaat tgaccacagt caccggtacc aatggtttgc caactgatga accatcatt | 1200 |
| gtcatcagaa caccaacaac agccactact gccatgacta caactcagcc atggaacgac | 1260 |
| acttttacct ctacatccac tgaaatgacc accgtcaccg gtaccaacgg tttgccaact | 1320 |
| gatgaaacca tcattgtcat cagaacacca acaacagcca ctactgctat gactacaact | 1380 |
| cagccatgga acgacacttt tacctctaca tccactgaaa tgaccaccgt caccggtacc | 1440 |
| aacggtttgc caactgatga accatcatt gtcatcagaa caccaacaac agccactact | 1500 |
| gccatgacta caactcagcc atggaacgac acttttacct ctacatccac tgaaatgacc | 1560 |
| accgtcaccg gtaccaatgg tttgccaact gatgagacca tcattgtcat cagaacacca | 1620 |
| acaacagcca ctactgccat gactacaact cagccatgga acgacacttt tacctctaca | 1680 |
| tccactgaaa tgaccaccgt caccggtacc aacggtttgc caactgatga accatcatt | 1740 |
| gtcatcagaa caccaacaac agccactact gccataacta caactgagcc atggaacagc | 1800 |
| acttttacct ctacttctac cgaattgacc acagtcaccg gtaccaatgg tttgccaact | 1860 |
| gatgagacca tcattgtcat cagaacacca acaacagcca ctactgccat gactacaact | 1920 |
| cagccatgga acgacacttt tacctctaca tccactgaaa tgaccaccgt caccggtacc | 1980 |
| aacggtttgc caactgatga accatcatt gtcatcagaa caccaacaac agccactact | 2040 |
| gccatgacta caactcagcc atggaacgac acttttacct ctacatccac tgaaatgacc | 2100 |
| accgtcaccg gtaccaacgg tttgccaact gatgagacca tcattgtcat cagaacacca | 2160 |
| acaacagcca ctactgccat gactacaact cagccatgga acgacacttt tacctctaca | 2220 |
| tccactgaaa tgaccaccgt caccggtacc aacggcgttc aactgacga aaccgtcatt | 2280 |
| gtcatcagaa ctccaactag tgaaggtcta atcagcacca ccactgaacc atggactggt | 2340 |
| actttcacct ctacatccac tgagatgacc accgtcaccg gtactaacgg tcaaccaact | 2400 |
| gacgaaaccg tgattgttat cagaactcca accagtgaag gtttggttac aaccaccact | 2460 |
| gaaccatgga ctggtacttt tacttctaca tctactgaaa tgaccaccat tactggaacc | 2520 |
| aacggcgttc aactgacga aaccgtcatt gtcatcagaa ctccaaccag tgaaggtcta | 2580 |
| atcagcacca ccactgaacc atggactggt acttttactt ctacatctac tgaaatgacc | 2640 |
| accattactg gaccaatgg tcaaccaact gacgaaaccg ttattgttat cagaactcca | 2700 |
| actagtgaag gtctaatcag caccaccact gaaccatgga ctggtacttt cacttctaca | 2760 |
| tctactgaaa tgaccaccgt caccggtacc aacggcgttc aactgacga aaccgtcatt | 2820 |
| gtcatcagaa ctccaaccag tgaaggtcta atcagcacca ccactgaacc atggactggc | 2880 |

-continued

```
actttcactt cgacttccac tgaggttacc accatcactg gaaccaacgg tcaaccaact    2940
gacgaaactg tgattgttat cagaactcca accagtgaag gtctaatcag caccaccact    3000
gaaccatgga ctggtacttt cacttctaca tctgctgaaa tgaccaccgt caccggtact    3060
aacggtcaac caactgacga aaccgtgatt gttatcagaa ctccaaccag tgaaggtttg    3120
gttacaacca ccactgaacc atggactggt acttttactt cgacttccac tgaaatgtct    3180
actgtcactg gaaccaatgg cttgccaact gatgaaactg tcattgttgt caaaactcca    3240
actactgcca tctcatccag tttgtcatca tcatcttcag acaaatcac cagctctatc     3300 acgtcttcgc gtccaattat tacccattc tatcctagca atggaacttc tgtgatttct     3360
tcctcagtaa tttcttcctc agtcacttct tctctattca cttcttctcc agtcatttct    3420
tcctcagtca tttcttcttc tacaacaacc tccacttcta tattttctga atcatctaaa    3480
tcatccgtca ttccaaccag tagttccacc tctggttctt ctgagagcga aacgagttca    3540
gctggttctg tctcttcttc ctctttatc tcttctgaat catcaaaatc tcctacatat      3600
tcttcttcat cattaccact tgttaccagt gcgacaacaa gccaggaaac tgcttcttca    3660
ttaccacctg ctaccactac aaaaacgagc gaacaaacca ctttggttac cgtgacatcc    3720
tgcgagtctc atgtgtgcac tgaatccatc tcccctgcga ttgtttccac agctactgtt    3780
actgttagcg gcgtcacaac agagtatacc acatggtgcc ctatttctac tacagagaca    3840
acaaagcaaa ccaaagggac aacagagcaa accacagaaa caacaaaaca aaccacggta    3900
gttacaattt cttcttgtga atctgacgta tgctctaaga ctgcttctcc agccattgta    3960
tctacaagca ctgctactat taacggcgtt actacagaat acacaacatg gtgtcctatt    4020
tccaccacag aatcgaggca acaaacaacg ctagttactg ttacttcctg cgaatctggt    4080
gtgtgttccg aaactgcttc acctgccatt gtttcgacgg ccacggctac tgtgaatgat    4140
gttgttacgg tctatcctac atggaggcca cagactgcga tgaagagtc tgtcagctct      4200 aaaatgaaca gtgctaccgg tgagacaaca accaatactt tagctgctga aacgactacc    4260
aatactgtag ctgctgagac gattaccaat actggagctg ctgagacgaa acagtagtc     4320 acctcttcgc tttcaagatc taatcacgct gaaacacaga cggcttccgc gaccgatgtg    4380
attggtcaca gcagtagtgt tgtttctgta tccgaaactg gcaacaccaa gagtctaaca    4440
agttccgggt tgagtactat gtcgcaacag cctcgtagca caccagcaag cagcatggta    4500
ggatatagta cagcttcttt agaaatttca acgtatgctg gcagtgccaa cagcttactg    4560
gccggtagtg gtttaagtgt cttcattgcg tccttattgc tggcaattat ttaa           4614
```

<210> SEQ ID NO 19
<211> LENGTH: 5857
<212> TYPE: DNA
<213> ORGANISM: Saccharomyces cerevisiae and E. coli
<220> FEATURE:
<221> NAME/KEY: promoter
<222> LOCATION: (1)..(452)
<223> OTHER INFORMATION: S. cerevisiae GAL1 promoter
<220> FEATURE:
<221> NAME/KEY: misc_feature
<223> OTHER INFORMATION: (476-495) E. coli T7 promoter/priming site
<220> FEATURE:
<221> NAME/KEY: misc_feature
<223> OTHER INFORMATION: (502-601) E. coli multiple cloning site
<220> FEATURE:
<221> NAME/KEY: misc_feature
<223> OTHER INFORMATION: (609-857) S. cerevisiae CYC1 transcription
      terminator
<220> FEATURE:

<221> NAME/KEY: misc_feature
<223> OTHER INFORMATION: (1039-1712) E. coli pMB1 (pUC-derived) origin
<220> FEATURE:
<221> NAME/KEY: gene
<222> LOCATION: (1857)..(2717)
<223> OTHER INFORMATION: E. coli ampicillin resistance gene
<220> FEATURE:
<221> NAME/KEY: gene
<222> LOCATION: (2735)..(3842)
<223> OTHER INFORMATION: S. cerevisiae URA3 gene
<220> FEATURE:
<221> NAME/KEY: misc_feature
<223> OTHER INFORMATION: (3846-5317) S. cerevisiae 2 micron origin
<220> FEATURE:
<221> NAME/KEY: misc_feature
<223> OTHER INFORMATION: (5385-5840) E. coli f1 origin
<220> FEATURE:
<221> NAME/KEY: misc_feature
<223> OTHER INFORMATION: (1-5857) Sequence of pYES2

<400> SEQUENCE: 19

```
acggattaga agccgccgag cgggtgacag ccctccgaag gaagactctc ctccgtgcgt      60
cctcgtcctc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcatt aaccacttta actaatactt tcaacatttt     360
cggtttgtat tacttcttat tcaaatgtaa taaaagtatc aacaaaaaat tgttaatata     420
cctctatact ttaacgtcaa ggagaaaaaa ccccggatcg gactactagc agctgtaata     480
cgactcacta tagggaatat taagcttggt accgagctcg gatccactag taacggccgc     540
cagtgtgctg gaattctgca gatatccatc acactggcgg ccgctcgagc atgcatctag     600
agggccgcat catgtaatta gttatgtcac gcttacattc acgccctccc cccacatccg     660
ctctaaccga aaaggaagga gttagacaac ctgaagtcta ggtccctatt tatttttttta    720
tagttatgtt agtattaaga acgttatttta tatttcaaat ttttcttttt tttctgtaca    780
gacgcgtgta cgcatgtaac attatactga aaaccttgct tgagaaggtt ttgggacgct    840
cgaaggcttt aatttgcggc cctgcattaa tgaatcggcc aacgcgcggg gagaggcggt    900
ttgcgtattg ggcgctcttc cgcttcctcg ctcactgact cgctgcgctc ggtcgttcgg    960
ctgcggcgag cggtatcagc tcactcaaag gcggtaatac ggttatccac agaatcaggg   1020
gataacgcag gaaagaacat gtgagcaaaa ggccagcaaa agcccaggaa ccgtaaaaag   1080
gccgcgttgc tggcgttttt ccataggctc cgcccccctg acgagcatca caaaaatcga   1140
cgctcaagtc agaggtggcg aaacccgaca ggactataaa gataccaggc gtttccccct   1200
ggaagctccc tcgtgcgctc tcctgttccg accctgccgc ttaccggata cctgtccgcc   1260
tttctccctt cgggaagcgt ggcgctttct catagctcac gctgtaggta tctcagttcg   1320
gtgtaggtcg ttcgctccaa gctgggctgt gtgcacgaac cccccgttca gcccgaccgc   1380
tgcgccttat ccggtaacta tcgtcttgag tccaacccgg taagacacga cttatcgcca   1440
ctggcagcag ccactggtaa caggattagc agagcgaggt atgtaggcgg tgctacagag   1500
ttcttgaagt ggtggcctaa ctacggctac actagaagga cagtatttgg tatctgcgct   1560
ctgctgaagc cagttacctt cggaaaaaga gttggtagct cttgatccgg caaacaaacc   1620
accgctggta gcggtggttt ttttgtttgc aagcagcaga ttacgcgcag aaaaaaagga   1680
tctcaagaag atcctttgat cttttctacg gggtctgacg ctcagtggaa cgaaaactca   1740
```

-continued

```
cgttaaggga ttttggtcat gagattatca aaaggatct tcacctagat ccttttaaat    1800
taaaaatgaa gttttaaatc aatctaaagt atatatgagt aaacttggtc tgacagttac    1860
caatgcttaa tcagtgaggc acctatctca gcgatctgtc tatttcgttc atccatagtt    1920
gcctgactcc ccgtcgtgta gataactacg atacgggagc gcttaccatc tggcccagt    1980
gctgcaatga taccgcgaga cccacgctca ccggctccag atttatcagc aataaaccag    2040
ccagccggaa gggccgagcg cagaagtggt cctgcaactt tatccgcctc cattcagtct    2100
attaattgtt gccgggaagc tagagtaagt agttcgccag ttaatagttt gcgcaacgtt    2160
gttggcattg ctacaggcat cgtggtgtca ctctcgtcgt ttggtatggc ttcattcagc    2220
tccggttccc aacgatcaag gcgagttaca tgatcccca tgttgtgcaa aaaagcggtt    2280
agctccttcg gtcctccgat cgttgtcaga agtaagttgg ccgcagtgtt atcactcatg    2340
gttatggcag cactgcataa ttctcttact gtcatgccat ccgtaagatg cttttctgtg    2400
actggtgagt actcaaccaa gtcattctga gaatagtgta tgcggcgacc gagttgctct    2460
tgcccggcgt caatacggga taatagtgta tcacatagca gaactttaaa agtgctcatc    2520
attggaaaac gttcttcggg gcgaaaactc tcaaggatct taccgctgtt gagatccagt    2580
tcgatgtaac ccactcgtgc acccaactga tcttcagcat cttttacttt caccagcgtt    2640
tctgggtgag caaaaacagg aaggcaaaat gccgcaaaaa agggaataag ggcgacacgg    2700
aaatgttgaa tactcatact cttccttttt caatgggtaa taactgatat aattaaattg    2760
aagctctaat ttgtgagttt agtatacatg catttactta taatacagtt ttttagtttt    2820
gctggccgca tcttctcaaa tatgcttccc agcctgcttt tctgtaacgt tcaccctcta    2880
ccttagcatc ccttcccttt gcaaatagtc ctcttccaac aataataatg tcagatcctg    2940
tagagaccac atcatccacg gttctatact gttgacccaa tgcgtctccc ttgtcatcta    3000
aacccacacc gggtgtcata atcaaccaat cgtaaccttc atctcttcca cccatgtctc    3060
tttgagcaat aaagccgata acaaaatctt tgtcgctctt cgcaatgtca acagtaccct    3120
tagtatattc tccagtagat agggagccct tgcatgacaa ttctgctaac atcaaaaggc    3180
ctctaggttc cttttgttact tcttctgccg cctgcttcaa accgctaaca ataacctgggc    3240
ccaccacacc gtgtgcattc gtaatgtctg cccattctgc tattctgtat acacccgcag    3300
agtactgcaa tttgactgta ttaccaatgt cagcaaattt tctgtcttcg aagagtaaaa    3360
aattgtactt ggcggataat gcctttagcg gcttaactgt gccctccatg aaaaatcag    3420
tcaagatatc cacatgtgtt tttagtaaac aaattttggg acctaatgct tcaactaact    3480
ccagtaattc cttggtggta cgaacatcca atgaagcaca caagtttgtt tgcttttcgt    3540
gcatgatatt aaatagcttg gcagcaacag gactaggatg agtagcagca cgttccttat    3600
atgtagcttt cgacatgatt tatcttcgtt cctgcaggt ttttgttctg tgcagttggg    3660
ttaagaatac tgggcaattt catgtttctt caacactaca tatgcgtata tataccaatc    3720
taagtctgtg ctccttcctt cgttcttcct tctgttcgga gattaccgaa tcaaaaaaat    3780
ttcaaagaaa ccgaaatcaa aaaaagaat aaaaaaaaaa tgatgaattg aattgaaaag    3840
ctagcttatc gatgataagc tgtcaaagat gagaattaat tccacggact atagactata    3900
ctagatactc cgtctactgt acgatacact tccgctcagg tccttgtcct ttaacgaggc    3960
cttaccactc ttttgttact ctattgatcc agctcagcaa aggcagtgtg atctaagatt    4020
ctatcttcgc gatgtagtaa aactagctag accgagaaag agactagaaa tgcaaaaggc    4080
```

-continued

```
acttctacaa tggctgccat cattattatc cgatgtgacg ctgcagcttc tcaatgatat      4140
tcgaatacgc tttgaggaga tacagcctaa tatccgacaa actgttttac agatttacga      4200
tcgtacttgt tacccatcat tgaattttga acatccgaac ctgggagttt tccctgaaac      4260
agatagtata tttgaacctg tataataata tatagtctag cgctttacgg aagacaatgt      4320
atgtatttcg gttcctggag aaactattgc atctattgca taggtaatct tgcacgtcgc      4380
atccccggtt cattttctgc gtttccatct tgcacttcaa tagcatatct ttgttaacga      4440
agcatctgtg cttcattttg tagaacaaaa atgcaacgcg agagcgctaa ttttcaaac       4500 aaagaatctg agctgcattt ttacagaaca gaaatgcaac gcgaaagcgc tattttacca      4560
acgaagaatc tgtgcttcat ttttgtaaaa caaaaatgca acgcgacgag agcgctaatt      4620
tttcaaacaa agaatctgag ctgcattttt acagaacaga atgcaacgc gagagcgcta      4680 ttttaccaac aaagaatcta tacttctttt tgttctaca aaatgcatc ccgagagcgc        4740 tatttttcta caaagcatc ttagattact tttttctcc tttgtgcgct ctataatgca        4800
gtctcttgat aacttttgc actgtaggtc cgttaaggtt agaagaaggc tactttggtg       4860
tctattttct cttccataaa aaagcctga ctccacttcc cgcgtttact gattactagc       4920
gaagctgcgg gtgcattttt tcaagataaa ggcatccccg attatattct ataccgatgt      4980
ggattgcgca actttgtga acagaaagtg atagcgttga tgattcttca ttggtcagaa       5040
aattatgaac ggtttcttct attttgtctc tatatactac gtataggaaa tgtttacatt      5100
ttcgtattgt tttcgattca ctctatgaat agttcttact acaatttttt tgtctaaaga      5160
gtaatactag agataaacat aaaaaatgta gaggtcgagt ttagatgcaa gttcaaggag      5220
cgaaaggtgg atgggtaggt tatataggga tatagcacag agatatatag caaagagata      5280
cttttgagca atgtttgtgg aagcggtatt cgcaatggga agctccaccc cggttgataa      5340
tcagaaaagc cccaaaaaca ggaagattgt ataagcaaat attaaattg taaacgttaa       5400 tattttgtta aaattcgcgt taaattttg ttaaatcagc tcattttta acgaatagcc        5460 cgaaatcggc aaaatccctt ataaatcaaa agaatagacc gagataggt tgagtgttgt      5520 tccagtttcc aacaagagtc cactattaaa gaacgtggac tccaacgtca aagggcgaaa     5580
aagggtctat cagggcgatg gcccactacg tgaaccatca ccctaatcaa gttttttggg    5640
gtcgaggtgc cgtaaagcag taaatcggaa gggtaaacgg atgcccccat ttagagcttg    5700
acggggaaag ccggcgaacg tgcgagaaa ggaagggaag aaagcgaaag gagcggggc       5760 tagggcggtg ggaagtgtag gggtcacgct gggcgtaacc accacaccg ccgcgcttaa     5820 tggggcgcta cagggcgcgt ggggatgatc cactagt                             5857
```

<210> SEQ ID NO 20
<211> LENGTH: 403
<212> TYPE: DNA
<213> ORGANISM: Trichoderma reesei
<220> FEATURE:
<221> NAME/KEY: misc_feature
<223> OTHER INFORMATION: (1-403) T. reesei hfb2 coding sequence
<220> FEATURE:
<221> NAME/KEY: intron
<222> LOCATION: (131)..(200)
<220> FEATURE:
<221> NAME/KEY: intron
<222> LOCATION: (287)..(358)

<400> SEQUENCE: 20

```
atgcagttct tcgccgtcgc cctcttcgcc accagcgccc tggctgctgt ctgccctacc      60
```

-continued

| | |
|---|---|
| ggcctcttct ccaaccctct gtgctgtgcc accaacgtcc tcgacctcat tggcgttgac | 120 |
| tgcaagaccc gtatgttgaa ttccaatctc tgggcatcct gacattggac gatacagttg | 180 |
| acttacacga tgctttacag ctaccatcgc cgtcgacact ggcgccatct tccaggctca | 240 |
| ctgtgccagc aagggctcca agcctctttg ctgcgttgct cccgtggtaa gtagtgctcg | 300 |
| caatggcaaa gaagtaaaaa gacatttggg cctgggatcg ctaactcttg atatcaaggc | 360 |
| cgaccaggct ctcctgtgcc agaaggccat cggcaccttc taa | 403 |

<210> SEQ ID NO 21
<211> LENGTH: 59
<212> TYPE: DNA
<213> ORGANISM: Artificial Sequence
<220> FEATURE:
<223> OTHER INFORMATION: Description of Artificial Sequence: PCR 5'
      primer

<400> SEQUENCE: 21
cggaggagct cgacgacttc gagcagcccg agctgcacgc aggctgtctg ccctaccgg    59

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: PCR 3'
      primer

<400> SEQUENCE: 22
tcattggatc cttagaaggt gccgatggc                                      29

<210> SEQ ID NO 23
<211> LENGTH: 679
<212> TYPE: DNA
<213> ORGANISM: Schizophyllum commune
<220> FEATURE:
<221> NAME/KEY: misc_feature
<223> OTHER INFORMATION: (1-679) SC3 coding sequence
<220> FEATURE:
<221> NAME/KEY: misc_feature
<223> OTHER INFORMATION: (1-92) 1st cDNA
<220> FEATURE:
<221> NAME/KEY: misc_feature
<223> OTHER INFORMATION: (146-183) 2nd cDNA
<220> FEATURE:
<221> NAME/KEY: misc_feature
<223> OTHER INFORMATION: (240-317) 3rd cDNA
<220> FEATURE:
<221> NAME/KEY: misc_feature
<223> OTHER INFORMATION: (374-469) 4th cDNA
<220> FEATURE:
<221> NAME/KEY: misc_feature
<223> OTHER INFORMATION: (524-586) 5th cDNA
<220> FEATURE:
<221> NAME/KEY: misc_feature
<223> OTHER INFORMATION: (635-679) 6th cDNA

<400> SEQUENCE: 23

| | |
|---|---|
| atgttcgccc gtctccccgt cgtgttcctc tacgccttcg tcgcgttcgg cgccctcgtc | 60 |
| gctgccctcc caggtggcca cccgggcacg acgtacgtcg acctctcacc gtcctctaat | 120 |
| gtcttgctga tgaagcccccg tatagcacgc cgccggttac gacgacggtg acggtgacca | 180 |
| cggtgagtag ctttctcgcc gtcgacgact cgaacgcatt ggctaatttt tgctcatagc | 240 |
| cgccctcgac gacgaccatc gccgccggtg gcacgtgtac tacggggtcg ctctcttgct | 300 |
| gcaaccaggt tcaatcggta cgtacatcaa agcggcacga ccaggcatct cagctgacgg | 360 |

```
ccacatcgta caggcgagca gcagccctgt taccgccctc ctcggcctgc tcggcattgt    420
cctcagcgac ctcaacgttc tcgttggcat cagctgctct cccctcactg tgagatcttt    480
ttgttcactg tcccaattac tgcgcactga cagactttgc caggtcatcg gtgtcggagg    540
cagcggctgt tcggcgcaga ccgtctgctg cgaaaacacc caattcgtat gtatactttc    600
catgcgtgtc cctttctccg ctaatcatct gtagaacggg ctgatcaaca tcggttgcac    660
ccccatcaac atcctctga                                                 679
```

<210> SEQ ID NO 24
<211> LENGTH: 63
<212> TYPE: DNA
<213> ORGANISM: Artificial Sequence
<220> FEATURE:
<223> OTHER INFORMATION: Description of Artificial Sequence: PCR 5'
      primer

<400> SEQUENCE: 24

```
actacacgga ggagctcgac gacttcgagc agcccgagct gcacgcaggg tggccacccg    60
ggc                                                                  63
```

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: PCR 3'
      primer

<400> SEQUENCE: 25

```
tcgtacggat cctcagagga tgttgatggg                                     30
```

<210> SEQ ID NO 26
<211> LENGTH: 43
<212> TYPE: DNA
<213> ORGANISM: Artificial Sequence
<220> FEATURE:
<223> OTHER INFORMATION: Description of Artificial Sequence: PCR 5'
      primer

<400> SEQUENCE: 26

```
ggaattccgc ggactgcgca tcatgaagtt cttcgccatc gcc                      43
```

<210> SEQ ID NO 27
<211> LENGTH: 80
<212> TYPE: DNA
<213> ORGANISM: Artificial Sequence
<220> FEATURE:
<223> OTHER INFORMATION: Description of Artificial Sequence: PCR 3'
      primer

<400> SEQUENCE: 27

```
tgaattccat atgttaggta ccaccggggc ccatgccggt agaagtagaa gccccgggag    60
caccgacggc ggtctggcac                                                80
```

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: PCR 5'
      primer

<400> SEQUENCE: 28

-continued tgaattcggt acccaggctt gctcaagcgt c                                            31

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: PCR 3'
      primer

<400> SEQUENCE: 29
tgaattccat atgtcacagg cactgagagt agta                                         34

<210> SEQ ID NO 30
<211> LENGTH: 48
<212> TYPE: DNA
<213> ORGANISM: Artificial Sequence
<220> FEATURE:
<223> OTHER INFORMATION: Description of Artificial Sequence: PCR 5'
      primer

<400> SEQUENCE: 30
gaattcggta ccctcgtccc tcgcggtccc gccgaagtga acctggtg                          48

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: PCR 3'
      primer

<400> SEQUENCE: 31
tgaattccat atgctaaccc cgtttcatct ccag                                         34

<210> SEQ ID NO 32
<211> LENGTH: 918
<212> TYPE: DNA
<213> ORGANISM: Trichoderma reesei
<220> FEATURE:
<221> NAME/KEY: terminator
<222> LOCATION: (1)..(918)
<223> OTHER INFORMATION: T. reesei hfb1 terminator

<400> SEQUENCE: 32
gatgcccgcc cggggtcaag gtgtgcccgt gagaaagccc acaaagtgtt gatgaggacc              60
atttccggta ctgggaaagt tggctccacg tgtttgggca ggtttgggca agttgtgtag             120
atattccatt cgtacgccat tcttattctc caatatttca gtacactttt cttcataaat             180
caaaaagact gctattctct ttgtgacatg ccggaaggga acaattgctc ttggtctctg             240
ttatttgcaa gtaggagtgg gagattcgcc ttagagaaag tagagaagct gtgcttgacc             300
gtggtgtgac tcgacgagga tggactgaga gtgttaggat taggtcgaac gttgaagtgt             360
atacaggatc gtctggcaac ccacggatcc tatgacttga tgcaatggtg aagatgaatg             420
acagtgtaag aggaaaagga aatgtccgcc ttcagctgat atccacgcca atgatacagc             480
gatataccctc caatatctgt gggaacgaga catgacatat ttgtgggaac aacttcaaac            540
agcgagccaa gacctcaata tgcacatcca aagccaaaca ttggcaagac gagagacagt             600
cacattgtcg tcgaaagatg gcatcgtacc caaatcatca gctctcatta tcgcctaaac             660
cacagattgt ttgccgtccc ccaactccaa aacgttacta caaaagacat gggcgaatgc             720
aaagacctga agcaaacccc tttttgcgac tcaattccct cctttgtcct cggaatgatg             780

| | |
|---|---:|
| atccttcacc aagtaaaaga aaaagaagat tgagataata catgaaaagc acaacggaaa | 840 |
| cgaaagaacc aggaaaagaa taaatctatc acgcaccttg tccccacact aaaagcaaca | 900 |
| gggggggtaa aatgaaat | 918 |

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: PCR 5'
    primer

<400> SEQUENCE: 33

| | |
|---|---:|
| gacctcgatg cccgcccggg gtcaag | 26 |

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: PCR 3'
    primer

<400> SEQUENCE: 34

| | |
|---|---:|
| gtcgacattt cattttaccc ccctcg | 26 |

<210> SEQ ID NO 35
<211> LENGTH: 1190
<212> TYPE: DNA
<213> ORGANISM: Trichoderma reesei
<220> FEATURE:
<221> NAME/KEY: promoter
<222> LOCATION: (1)..(1190)
<223> OTHER INFORMATION: T. reesei hfb2 promoter

<400> SEQUENCE: 35

| | |
|---|---:|
| ctcgagcagc tgaagcttgc atgcctgcat cctttgtgag cgactgcatc cattttgcac | 60 |
| acactgccgt cgacgtctct cttccgacct tggccagctg acaagcaac acaccaatga | 120 |
| cgctttgtat tattagagta tatgcaagtc tcaggactat cgactcaact ctacccaccg | 180 |
| aggacgatcg cggcacgata cgccctcgtt ctcattggcc caagcagacc aactgcccct | 240 |
| ggagcaagat tcagcccaag ggagatggac ggcagggcac gccaggcccc caccaccaag | 300 |
| ccactcccctt tggccaaatc agcttgcatg tcaagagaca tcgagctgtg ccttgaaatt | 360 |
| actaacaacc agggatggga aacgaagcct gcttttggaa agacaacaat gagagagaga | 420 |
| gagagaggga gagagacaat gagtgccaca aacctggtag tgctccgcca atgcgtctga | 480 |
| aatgtcacat ccgagtcttg gggcctctgt gagaatgtcc agagtaatac gtgttttgcg | 540 |
| aatagtcctc tttcttgagg actggatacc tacgatacc ttttgagtt gatgcggtgc | 600 |
| tttcgaagta ttatctggag gatagaagac gtctaggtaa ctacacaaaa ggcctatact | 660 |
| ttggggagta gcccaacgaa aggtaactcc tacggcctct tagagccgtc atagatccta | 720 |
| cagcctcttg gagccgtcat agatcacatc tgtgtagacc gacattctat gaataatcat | 780 |
| ctcatcatgg ccacatacta ctacatacgt gtctctgcct acctgacatg tagcagtggc | 840 |
| caagacacca aggcccagc atcaagcctc cctacctatc ccttccattg tacagcggca | 900 |
| gagagattgc gatgagccct ctccctacct acagacggct gacaatgtcc gtataccacc | 960 |
| agccaacgtg atgaaaacaa ggacatgagg aacagcctgc gagagctgga agatgaagag | 1020 |
| ggccagaaaa aaaagtataa agaagacctc gattcccgcc atccaacaat cttttccatc | 1080 |

```
ctcatcagca cactcatcta caaccatcac cacattcact caactcctct ttctcaactc    1140
tccaaacaca aacattcttt gttgaatacc aaccatcacc acctttcaag              1190
```

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: PCR 5'
      primer

<400> SEQUENCE: 36

```
aagcttgcat gcctgcatcc                                                 20
```

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: PCR 3'
      primer

<400> SEQUENCE: 37

```
ccatggtgaa aggtggtgat ggttgg                                          26
```

<210> SEQ ID NO 38
<211> LENGTH: 13
<212> TYPE: PRT
<213> ORGANISM: Trichoderma reesei
<220> FEATURE:
<221> NAME/KEY: misc_feature
<223> OTHER INFORMATION: vild type T. reesei EGI peptide linker

<400> SEQUENCE: 38

Val Pro Arg Gly Ser Ser Ser Gly Thr Ala Pro Gly Gly
 1               5                  10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: modified
      CBHII linker

<400> SEQUENCE: 39

Gly Ser Ser Ser Gly Thr Ala Pro Gly Gly
 1               5                  10

<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence:
      Met/Thrombin linker

<400> SEQUENCE: 40

Pro Gly Arg Pro Val Leu Thr Gly Pro Gly Met Gly Thr Ser Thr Ser
 1               5                  10                  15

Ala Gly Pro

<210> SEQ ID NO 41
<211> LENGTH: 13
<212> TYPE: PRT

```
<213> ORGANISM: Artificial Sequence
<220> FEATURE:
<223> OTHER INFORMATION: Description of Artificial Sequence:
      Met-containing linker

<400> SEQUENCE: 41

Pro Gly Ala Ser Thr Ser Thr Gly Met Gly Pro Gly Gly
 1               5                  10

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: linker
      containing the thrombin cleavage site

<400> SEQUENCE: 42

Gly Thr Leu Val Pro Arg Gly Pro Ala Gly Val Asn Leu Val
 1               5                  10

<210> SEQ ID NO 43
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide NheIBgIIINheI of the pTNS15 plasmid

<400> SEQUENCE: 43
gctagagatc tctagc                                                    16

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: synthetic
      peptide AocIXbaIAocI of the pTNS15 plasmid

<400> SEQUENCE: 44

Ala Ser Gly Ala Ser Arg Ala Ser Gly
 1               5

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: synthetic
      oligonucleotide AocIXbaIAocI of the pTNS15 plasmid

<400> SEQUENCE: 45
gcctcaggag cctctagagc ttcagga                                        27

<210> SEQ ID NO 46
<211> LENGTH: 20
<212> TYPE: PRT
<213> ORGANISM: Trichoderma reesei

<400> SEQUENCE: 46

Ala Asn Ala Phe Cys Pro Glu Gly Leu Leu Tyr Thr Asn Pro Leu Cys
 1               5                  10                  15

Cys Asp Leu Leu
            20
```

OLIGONUCLEOTIDES FOR NUCLEIC ACID AMPLIFICATION AND FOR THE DETECTION OF *MYCOBACTERIUM TUBERCULOSIS*

This application is a divisional of U.S. application Ser. No. 08/345,861, filed Nov. 28, 1994, now U.S. Pat. No. 5,766,849, which is a continuation of U.S. application Ser. No. 07/925,405, filed Aug. 4, 1992, now abandoned, which is a continuation-in-part of U.S. application Ser. No. 07/855,732, filed Mar. 19, 1992, now U.S. Pat. No. 5,399,491, which is a continuation-in-part of U.S. application Ser. No. 07/550,837, filed Jul. 10, 1990, now U.S. Pat. No. 5,480,784, which is a continuation-in-part of U.S. application Ser. No. 07/379,501, filed Jul. 11, 1989, now abandoned, all of which applications are hereby incorporated by reference herein in their entirety.

FIELD OF THE INVENTION

This invention relates to methods for increasing the number of copies of a specific nucleic acid sequence or "target sequence" which may be present either alone or as a component, large or small, of a homogeneous or heterogeneous mixture of nucleic acids. The mixture of nucleic acids may be that found in a sample taken for diagnostic testing, environmental testing, for research studies, for the preparation of reagents or materials, for other processes such as cloning, or for other purposes.

The selective amplification of specific nucleic acid sequences is of value in increasing the sensitivity of diagnostic and environmental assays while maintaining specificity; increasing the sensitivity, convenience, accuracy and reliability of a variety of research procedures; and providing ample supplies of specific oligonucleotides for various purposes.

The present invention is particularly suitable for use in environmental and diagnostic testing due to the convenience with which it may be practiced.

BACKGROUND OF THE INVENTION

The detection and/or quantitation of specific nucleic acid sequences is an increasingly important technique for identifying and classifying microorganisms, diagnosing infectious diseases, detecting and characterizing genetic abnormalities, identifying genetic changes associated with cancer, studying genetic susceptibility to disease, and measuring response to various types of treatment. Such procedures have also found expanding uses in detecting and quantitating microorganisms in foodstuffs, environmental samples, seed stocks, and other types of material where the presence of specific microorganisms may need to be monitored. Other applications are found in the forensic sciences, anthropology, archaeology, and biology where measurement of the relatedness of nucleic acid sequences has been used to identify criminal suspects, resolve paternity disputes, construct genealogical and phylogenetic trees, and aid in classifying a variety of life forms.

A common method for detecting and quantitating specific nucleic acid sequences is nucleic acid hybridization. This method is based on the ability of two nucleic acid strands that contain complementary or essentially complementary sequences to specifically associate, under appropriate conditions, to form a double-stranded structure. To detect and/or quantitate a specific nucleic acid sequence (known as the "target sequence"), a labelled oligonucleotide (known as a "probe") is prepared that contains sequences complementary to those of the target sequence. The probe is mixed with a sample suspected of containing the target sequence, and conditions suitable for hybrid formation are created. The probe hybridizes to the target sequence if it is present in the sample. The probe-target hybrids are then separated from the single-stranded probe in one of a variety of ways. The amount of label associated with the hybrids is then measured as an indication of the amount of target sequence in the sample.

The sensitivity of nucleic acid hybridization assays is limited primarily by the specific activity of the probe, the rate and extent of the hybridization reaction, the performance of the method for separating hybridized and unhybridized probe, and the sensitivity with which the label can be detected. The most sensitive procedures may lack many of the features required for routine clinical and environmental testing such as speed, convenience, and economy. Furthermore, their sensitivities may not be sufficient for many desired applications.

As a result of the interactions among the various components and component steps of this type of assay, there is almost always an inverse relationship between sensitivity and specificity. Thus, steps taken to increase the sensitivity of the assay (such as increasing the specific activity of the probe) may result in a higher percentage of false positive test results. The linkage between sensitivity and specificity has been a significant barrier to improving the sensitivity of hybridization assays. One solution to this problem would be to specifically increase the amount of target sequence present using an amplification procedure. Amplification of a unique portion of the target sequence without amplification of a significant portion of the information encoded in the remaining sequences of the sample could give an increase in sensitivity while at the same time not compromising specificity.

A method for specifically amplifying nucleic acid sequences termed the "polymerase chain reaction" or "PCR" has been described by Mullis et al. (See U.S. Pat. Nos. 4,683,195, 4,683,202 and 4,800,159 and European patent applications 86302298.4, 86302299.2, and 87300203.4 and *Methods in Enzymology*, Volume 155, 1987, pp. 335–350.) The procedure uses repeated cycles of primer dependent nucleic acid synthesis occurring simultaneously using each strand of a complementary sequence as a template. The sequence that is amplified is defined by the locations of the primer molecules that initiate synthesis. The primers are complementary to the 3'-end portion of the target sequence or its complement and must complex with those sites in order for nucleic acid synthesis to begin. After extension product synthesis, the strands are separated, generally by thermal denaturation, before the next synthesis step. In the PCR procedure, copies of both strands of a complementary sequence are synthesized.

The strand separation step used in PCR to separate the newly synthesized strands at the conclusion of each cycle of the PCR reaction is often thermal denaturation. As a result, either a thermostable enzyme is required or new enzyme must be added between thermal denaturation steps and the initiation of the next cycle of DNA synthesis. The requirement of repeated cycling of reaction temperature between several different and extreme temperatures is a disadvantage of the PCR procedure. In order to make the PCR convenient, programmable thermal cycling instruments are required.

The PCR procedure has been coupled to RNA transcription by incorporating a promoter sequence into one of the primers used in the PCR reaction and then, after amplification by the PCR procedure for several cycles, using the double-stranded DNA as template for the transcription of single-stranded RNA. (See, e.g., Murakawa et al., DNA 7:287–295 (1988).)

Other methods for amplification of a specific nucleic acid sequence comprise a series of primer hybridization, extending and denaturing steps to provide an intermediate double stranded DNA molecule containing a promoter sequence through the use of a promoter sequence-containing primer. The double stranded DNA is used to produce multiple RNA copies of the target sequence. The resulting RNA copies can be used as target sequences to produce further copies, and multiple cycles can be performed. (See, e.g., Burg, et al., WO 89/1050; Gingeras, et al., WO 88/10315 (sometimes called "transcription amplification system" or TAS); EPO Application No. 89313154 to Kacian and Fultz; EPO Application No. 88113948.9 to Davey and Malek; Malek, et al. WO91/02818.)

Walker, et al., Proc. Natl. Acad. Sci. (USA) 89:392–396 (January 1992), not admitted to be prior art, describes an oligonucleotide driven amplification method for use with a DNA template, using a restriction endonuclease to produce the initial target sequences and an enzyme to nick the DNA/DNA complex in order to enable an extension reaction and therefore amplification. Becker, et al., EPO Application No. 88306717.5, describes an amplification method in which a primer is hybridized to the target sequence and the resulting duplex is cleaved prior to the extension reaction and amplification; in the case where the primer extends past the region of hybridization, it requires cleavage prior to the extension and the primer must be blocked at its 3'-end to prevent any unwanted extension reactions from occurring prior to amplification. Urdea, WO 91/10746, describes a signal amplification method that incorporates a T7 promoter sequence.

Other methods of amplifying nucleic acid include the ligase chain reaction (LCR), described in European Patent Application No. 320,308, in which at least four separate oligoprobes are used; two of the oligoprobes hybridize to opposite ends of the same target strand in appropriate orientation such that the third and fourth oligoprobes may hybridize with the first and second oligoprobes to form, upon ligation, connected probes that can be denatured and detected. Another method is that described in EPO Application No. 0 427 073 A2, published May 15, 1991 and not admitted to be prior art, in which a palindromic probe able to form a hairpin and having a functional promoter region in the hairpin is hybridized to a target sequence, then ligated to another oligonucleotide hybridized to the target sequence such that specific RNA transcripts may be made.

Relatively large amounts of certain RNAs may be made using a recombinant single-stranded RNA molecule having a recognition sequence for the binding of an RNA-directed polymerase, preferably Qβ replicase. (See, e.g., U.S. Pat. No. 4,786,600 to Kramer, et al.) A number of steps are required to insert the specific sequence into a DNA copy of the variant molecule, clone it into an expression vector, transcribe it into RNA and then replicate it with Qβ replicase.

Definitions

As used herein, the following terms have the following meanings unless expressly indicated to the contrary.

A. Nucleic Acid.

"Nucleic acid" means either RNA or DNA, along with any nucleotide analogues or other molecules that may be present in the sequence and that do not prevent performance of the present invention.

B. Template.

A "template" is a nucleic acid molecule that is able to be copied by a nucleic acid polymerase. A template may be either RNA or DNA, and may be any of single-stranded, double-stranded or partially double-stranded, depending on the polymerase. The synthesized copy is complementary to the template. In this invention, the term copies also includes nucleic acid having the equivalent RNA or DNA sequence to a template, which are commonly referred to as homologous sequences in the art.

C. Primer.

A "primer" is an oligonucleotide that is complementary to a template that hybridizes with the template to give a primer/template complex for initiation of synthesis by a DNA polymerase, such as a reverse transcriptase, and which is extended by the addition of covalently bonded bases linked to its 3' end that are complementary to the template. The result is a primer extension product. Virtually all DNA polymerases (including reverse transcriptases) that are known require complexing of an oligonucleotide to a single-stranded template ("priming") to initiate DNA synthesis. Under appropriate circumstances, a primer may be a part of a promoter-primer. Such primers are generally between 10 and 100 bases in length, preferably between 20 and 50 bases in length.

D. Promoter or Promoter Sequence.

A "promoter" or "promoter sequence" is a specific nucleic acid sequence that is recognized by a DNA-dependent RNA polymerase ("transcriptase") as a signal to bind to a nucleic acid molecule and begin the transcription of RNA at a specific site. For binding, such transcriptases generally require that the promoter and its complement be double-stranded; the template portion need not be double-stranded. Individual DNA-dependent RNA polymerases recognize a variety of different promoter sequences that can vary markedly in their efficiency of promoting transcription. When an RNA polymerase binds to a promoter sequence to initiate transcription, that promoter sequence is not part of the sequence transcribed. Thus, the RNA transcripts produced thereby will not include the promoter sequence.

E. Promoter-primer.

A promoter-primer comprises a promoter and a primer. It is an oligonucleotide that is sufficiently complementary to the 3'-end of a target nucleic acid sequence to complex at or near the 3'-end of that target nucleic acid sequence, which means that the promoter-primer complexes near enough the end of the target sequence to allow amplification of enough of the target sequence that the requirements of the assay, testing, cloning or other use for the amplified nucleic acid are met. The promoter-primer is used as a template to create a complementary nucleic acid sequence extending from the 3'-end (also known as the 3' terminus) of a target nucleic acid sequence, to result in a generally double stranded promoter, subject to any denaturing or enzymatic activity that may disrupt the double strand. Such promoter-primers are generally between 40 and 100 bases in length, preferably between 40 and 60 bases.

A DNA- or RNA-dependent DNA polymerase also creates a complementary strand to the target nucleic acid molecule, using the target sequence as a template.

F. Modified Primer or Promoter-primer.

The 3'-end of the primer or promoter-primer may be modified, or blocked, so as to prevent or reduce the rate and/or extent of an extension reaction from proceeding therefrom. A primer or promoter-primer having both modified and unmodified members consists of essentially the same nucleic acid sequence for the purposes of the present invention. In other words, the modified primer or promoter-primer does not contain a different complexing sequence (primer) in that both the modified and unmodified oligonucleotide hybridize in effectively the same position (plus or minus about ten bases) on the target nucleic acid sequence. Also, the modified promoter-primer does not contain a different recognition sequence (promoter) from the unmodified promoter-primer. This means that, within about 10 bases, the modified and unmodified primers or promoter-primers are the same, are recognized by the same RNA polymerase, and hybridize to more or less the same target sequence (although not necessarily at precisely the same position). In a preferred embodiment, the modified and unmodified primers or promoter-primers are identical except for the modification.

The 3'-end of the target complementary portion of a primer or promoter-primer can be modified in a variety of ways well known to those skilled in the art. Appropriate modifications to a promoter-primer can include addition of ribonucleotides, 3' deoxynucleotide residues, (e.g., cordycepin (CO, Glen Research)), 3',2'-dideoxy nucleotide residues, modified nucleotides with nonphosphodiester backbone linkages (such as phosphorothioates), and non-nucleotide linkages such as described in Arnold, et al., (PCT US 88/03173) (RS) or alkane-diol modifications (Wilk et al. Nuc. Acids Res. 18:2065, 1990) (RP), or the modification may simply consist of one or more nucleotide residues 3' to the hybridizing sequence that are uncomplementary to the target nucleic acid. Of course, other effective modifications are possible as well.

A mixture of modified and unmodified oligonucleotides may be used in an amplification reaction, and a broad range of ratios of modified to unmodified oligonucleotide (e.g., from 1:1 to 1,000:1) can be used. A mixture of oligonucleotides with different 3' modifications may also be used.

G. Plus (+) and Minus (−) Strand(s).

Discussions of nucleic acid synthesis are greatly simplified and clarified by adopting terms to name the two complementary strands of a nucleic acid duplex. Traditionally, the strand encoding the sequences used to produce proteins or structural RNAs was designated as the "plus" strand and its complement the "minus" strand. It is now known that in many cases, both strands are functional, and the assignment of the designation "plus" to one and "minus" to the other must then be arbitrary. Nevertheless, the terms are very useful for designating the sequence orientation of nucleic acids and will be employed herein for that purpose, with the "plus" strand denominating the original target sequence strand that is complexed with the first primer or promoter-primer.

H. Target Nucleic Acid Sequence, Target Sequence.

A "target nucleic acid sequence," or "target sequence," has a desired nucleic acid sequence to be amplified, and may be either single-stranded or double-stranded and may include other sequences 5' or 3' of the sequences to be amplified which may or may not be amplified.

The target nucleic acid sequence includes the complexing sequences to which the promoter-primer hybridizes during performance of the present invention. Where the target nucleic acid sequence is originally single-stranded, the term refers to either the (+) or (−) strand, and will also refer to the sequence complementary to the target sequence. Where the target nucleic acid sequence is originally double-stranded, the term refers to both the (+) and (−) strands.

I. DNA-Dependent DNA Polymerase.

A "DNA-dependent DNA polymerase" is an enzyme that synthesizes a complementary DNA copy from a DNA template. An example is bacteriophage T7 DNA polymerase. All known DNA-dependent DNA polymerases require a complementary primer, which can be RNA or DNA, or a copolymer, to initiate synthesis. It is known that under suitable conditions certain DNA-dependent DNA polymerases may synthesize a complementary DNA copy from an RNA template.

J. DNA-Dependent RNA Polymerase (Transcriptase).

A "DNA-dependent RNA polymerase" or "transcriptase" is an enzyme that synthesizes multiple RNA copies from a double-stranded or partially-double stranded DNA molecule having a (usually double-stranded) promoter sequence. It should be noted that the present invention includes single stranded promoter sequences in the promoter-primer, along with the RNA polymerases that recognize them. The RNA molecules ("transcripts") are synthesized in the 5'→3' direction of the RNA molecule, beginning at a specific position just downstream of the promoter. Examples of transcriptases are the DNA-dependent RNA polymerases from bacteriophages T7, T3, and SP6.

K. RNA-Dependent DNA Polymerase (Reverse Transcriptase).

An "RNA-dependent DNA polymerase" or "reverse transcriptase" is an enzyme that synthesizes a complementary DNA copy from an RNA template. All known reverse transcriptases also have the ability to make a complementary DNA copy from a DNA template; thus, they are both RNA- and DNA-dependent DNA polymerases. A primer is required to initiate synthesis with either the RNA or DNA templates.

L. RNAse H.

An "RNAse H" is an enzyme that degrades the RNA portion of an RNA:DNA duplex. RNAse H's may be endonucleases or exonucleases. Avian myeloblastosis virus and Moloney murine leukemia virus reverse transcriptases contain an RNAse H activity in addition to their polymerase activity. Some cloned reverse transcriptases lack RNAse H activity. There are also sources of RNAse H available without an associated polymerase activity. The degradation may result in separation of RNA from an RNA:DNA complex. Alternatively, the RNAse H may simply cut the RNA at various locations such that portions of the RNA melt off or permit enzymes to unwind portions of the RNA, or the RNA fragments generated may serve as primers for extension by a polymerase.

M. Hybridize, Complex.

The terms "hybridize" and "complex" refer to the formation of duplexes between nucleotide sequences that are sufficiently complementary to form duplexes (or "complexes") via Watson-Crick base pairing. Where a promoter-primer or primer "hybridizes" with target (template), such complexes (or hybrids) are sufficiently stable to serve the priming function required by a DNA polymerase to initiate DNA synthesis.

N. Specificity

Specificity is a characteristic of a nucleic acid sequence that describes its ability to distinguish between target and non-target sequences, dependent on sequence and assay conditions.

SUMMARY OF THE INVENTION

The present invention is directed to a novel, autocatalytic method of synthesizing multiple copies of a target nucleic acid sequence (i.e., the method cycles automatically without the need to modify reaction conditions such as temperature, pH, or ionic strength).

The present invention features treating a target sequence with a first oligonucleotide (that has a complexing sequence sufficiently complementary to a 3'-end portion of the target sequence to hybridize therewith (this alone is termed a primer), and that has a sequence 5' to the complexing sequence that includes a sequence which, in double-stranded form, acts as a promoter for an RNA polymerase (this arrangement is termed a promoter-primer)), and a second oligonucleotide (which is a primer or promoter-primer that has a complexing sequence sufficiently complementary to the complement of the target sequence to hybridize therewith), under conditions in which an oligonucleotide/target sequence complex may be formed and DNA and RNA synthesis may occur. In this invention, one or both of the first and second oligonucleotides is a mixture of a blocked and an unblocked oligonucleotide sequence (blocked oligonucleotides have a modified 3' end to prevent or reduce the rate and/or extent of primer extension by a DNA polymerase), or a mixture of oligonucleotides with different 3' modifications. Such a mixture significantly enhances the efficiency of the specific amplification reaction compared to use of only blocked or only unblocked oligonucleotides. The ratio of such oligonucleotides can be varied dependent upon the specific template sequence to be amplified, but generally is between 1:1 and 1000:1 blocked to unblocked. The invention does not require that the target sequence have defined 3'- or 5'-ends.

One aspect of the invention includes (a) treating a target sequence with a first promoter-primer oligonucleotide that has a complexing sequence sufficiently complementary to a 3'-end portion of the target sequence to hybridize therewith, and that has a sequence 5' to the complexing sequence that includes a sequence which, in double-stranded form, acts as a promoter for an RNA polymerase, under conditions in which an oligonucleotide/target sequence complex may be formed and DNA synthesis may be initiated by an appropriate polymerase (e.g., a DNA polymerase), (b) incubating the first oligonucleotide/target complex under extension reaction conditions so that the 3'-end of the target may be extended to produce a hybrid template for an RNA polymerase; and (c) incubating the hybrid template under conditions in which multiple RNA copies of the target sequence may be produced using an RNA polymerase that recognizes the promoter sequence. The invention also includes generation of a 3'-end of an RNA target sequence in step (b) by the action of an enzyme that selectively degrades the RNA portion of an RNA:DNA hybrid (e.g., RNase H). The RNA so produced may autocatalytically cycle to produce more product.

In other methods, the invention features (a) contacting a nucleic acid (e.g., RNA or DNA) target sequence with a first oligonucleotide primer or promoter-primer under conditions in which a first oligonucleotide/target sequence complex is formed such that DNA synthesis may be initiated by an appropriate polymerase (e.g., a DNA polymerase), (b) incubating the first oligonucleotide under extension reaction conditions so that the target may be used by the polymerase as a template to give a first DNA extension product complementary to the target (if the first primer is not blocked); (c) if the target is an RNA molecule, separating the DNA extension product from the RNA target using an enzyme that selectively degrades the RNA target, or if the target is a DNA molecule, separating the two DNA strands (e.g., by heating at 90–100° C., or by other means); (d) contacting the DNA extension product with a second oligonucleotide that includes a primer or a promoter-primer, and that has a complexing sequence sufficiently complementary to the 3'-end portion of the DNA extension product to hybridize therewith under conditions in which a second oligonucleotide/extension product complex is formed and DNA synthesis may be initiated as above, depending on any blocking molecules on this primer. In this invention, if the first oligonucleotide is not a promoter-primer, then the second oligonucleotide is a promoter-primer, which means the second oligonucleotide has a sequence 5' to the complexing sequence that includes a promoter sequence for an RNA polymerase. In addition, the first and/or second oligonucleotides consist of either a mixture of a blocked and an unblocked oligonucleotide, or a mixture of oligonucleotides with different 3' modifications.

The amplification reaction is performed in a mixture consisting essentially of the necessary reactants and reagents. However, such a mixture may also contain enzymes or other substituents that do not qualitatively affect the amplification of the invention (e.g., the mechanism of the reaction). Such substituents may affect the amount of amplification observed. For example, the mixture may contain other promoter-primers for the same target sequence, or may contain "helper" oligonucleotides. Such helper oligonucleotides are used in a manner similar to the hybridization helper probes described by Hogan et al., U.S. Pat. No. 5,030,557 (hereby incorporated by reference herein), namely by aiding binding of the promoter-primer to its target nucleic acid, even if that target nucleic acid has significant secondary structure. Despite the similarity in use of such helper oligonucleotides, it was surprising that such helper oligonucleotides could be used in an amplification protocol without adverse effect on the efficiency of the procedure.

The first oligonucleotide may be a promoter-primer and the second oligonucleotide may be a primer, or vice versa, or both the first and second oligonucleotides may be promoter-primers, with either identical promoters (in the sense that the promoters are recognized by the same RNA polymerase) or different promoters. Use of different promoters is particularly useful when the amplified nucleic acid will be used for cloning. The first and second oligonucleotides and the RNA produced from the target sequence may then be used to autocatalytically synthesize multiple copies (by which is meant both complementary and homologous nucleic acid sequences) of the target sequence.

The modified primer or promoter-primer of the present invention consists essentially of a single nucleic acid sequence that has a modification at or near (within 3 bases) the 3'-end of the given primer or promoter-primer that alters (decreases or blocks) extension of the primer on a template by a DNA polymerase. Preferably this modified primer or promoter-primer is mixed with an unmodified primer or promoter-primer consisting essentially of the same nucleic acid sequence, along with one or more other primers or promoter-primers of a different nucleic acid sequence (that may also be a mixture of blocked and unblocked oligonucleotides). The invention also includes use of mixtures of primers and promoter-primers with more than one modification at or near their 3'-ends.

In addition, in another aspect of the present invention, where the sequence sought to be amplified is DNA, use of an appropriate preliminary procedure may enhance generation of RNA copies that may then be amplified according to the present invention. Accordingly, the present invention is also directed to preliminary procedures for use in conjunction with the amplification method of the present invention that not only can increase the number of copies to be amplified, but also can provide RNA copies of a DNA sequence for amplification.

In a further aspect, the invention features generation of a defined 5' end (i.e., one of known sequence) in an RNA target sequence by treating the RNA with a DNA oligonucleotide which hybridizes near the second primer binding site and thereby forms a substrate for RNAse H. This substrate is then cleaved by RNAse H to define the 5' end of the RNA target, which can be amplified as discussed above.

In another aspect, the present invention involves cooperative action of a DNA polymerase (such as a reverse transcriptase) and a DNA-dependent RNA polymerase (transcriptase) with an enzymatic hybrid-separation step to produce products that may themselves be used to produce additional product, thus resulting in an autocatalytic reaction without requiring manipulation of reaction conditions, such as in thermal cycling. Further, in some embodiments of the present invention that include a preliminary procedure, all but the initial step(s) of the preliminary procedure are carried out at one temperature.

The present invention may be used as a component of assays to detect and/or quantitate specific nucleic acid target sequences in clinical, environmental, forensic, and similar samples or to produce large numbers of copies of DNA and/or RNA of a specific target sequence for a variety of uses. These methods may also be used to produce multiple DNA copies of a DNA target for cloning, or to generate probes, or to produce RNA and DNA copies for sequencing.

In one example of a typical assay, a sample (including RNA or DNA target) to be amplified is mixed with a buffer concentrate containing the buffer, salts (e.g., divalent cations such as magnesium), nucleotide triphosphates, primers and/or promoter-primers (blocked and/or unblocked), a thiol reducing agent such as dithiothreitol, and a polycation such as spermidine. The reaction is then optionally incubated near 100° C. to denature any secondary structure. After cooling to room temperature (about 20° C.), enzymes containing DNA and RNA dependent DNA polymerase activity, RNAse H activity and DNA dependent RNA polymerase activity are added and the mixture is incubated for about 10 minutes to four hours at 37° C. to 42° C. The reaction can then be assayed by adding a luminescently-labelled probe, incubating 10 to 30 minutes at 60° C., adding a solution to selectively hydrolyze the label on unhybridized probe, incubating the reaction for 5 to 10 minutes at 60° C., and measuring the remaining chemiluminescence in a luminometer. (See, e.g., Arnold, et al., PCT/US88/03195 (filed Sep. 21, 1988, published Mar. 23, 1989) the disclosure of which is incorporated herein by reference and is referred to as "HPA".) The products of the invention may be used in many other assay systems known to those skilled in the art.

Optionally, a DNA target without a defined 3'-end, can be incubated near 100° C. to denature any secondary structure and cooled to room temperature. Reverse transcriptase is added and the reaction mixture is incubated for 12 minutes at 42° C. The reaction is again denatured near 100° C., this time to separate the primer extension product from the DNA template. After cooling, enzymes with DNA and RNA dependent DNA polymerase activity, RNAse H activity and DNA dependent RNA polymerase are added and the reaction is incubated for 10 minutes to four hours at 37° C.–42° C.

For a DNA target, a defined 3'-end can be created by use of a restriction endonuclease. A defined 3'-end may also be generated by other means known in the art.

Yet another aspect of the invention features a composition consisting essentially of a first and a second oligonucleotide of opposite sense and able to hybridize at or near the 3'-end of a target nucleic acid sequence and its complement, respectively, wherein one of the oligonucleotides is a promoter-primer and the other may be either a primer or a promoter-primer, and one or both of the oligonucleotides consists essentially of a mixture of a single nucleic acid sequence having either a modified or an unmodified 3'-end, a DNA-dependent DNA polymerase, an RNA-dependent DNA polymerase, and an RNA polymerase, wherein the mixture allows amplification at effectively constant pH, concentration and temperature (i.e., none of the recited conditions need be actively changed by the user). The composition may also include an RNAse H activity and/or other components described herein.

In other aspects, the invention features kits containing oligonucleotides including specific sequences useful in this amplification method, or in other amplification methods, such as those described above. Such sequences include those listed in the SEQUENCE LISTING, and may be attached to other sequences recognized by an enzyme (such as a polymerase, or restriction endonuclease). In particular, these oligonucleotides are useful for amplifying *Mycobacterium* nucleic acid, e.g., that of *M. tuberculosis*, and may have modified 3'-ends as discussed above.

The materials used in the present invention may be incorporated as part of diagnostic kits or other kits for use in diagnostic procedures, or other procedures, and the invention is adaptable to multi-well technology which may be provided in kit format.

BRIEF DESCRIPTION OF THE DRAWINGS

FIG. 1 shows the structure of the alkane-diol modification referred to as RP.

DETAILED DESCRIPTION OF THE INVENTION

In accordance with the present invention, a novel method, composition and kit are provided for the amplification of specific nucleic acid target sequences for use in assays for the detection and/or quantitation of specific nucleic acid target sequences or for the production of large numbers of copies of DNA and/or RNA of specific target sequences for a variety of uses.

The present invention advantageously provides an amplification method that synthesizes RNA copies of a target sequence by use of a mixture of blocked and unblocked promoter-primers, or promoter-primers with different 3' modifications, consisting essentially of the same nucleic acid sequence in a ratio that provides for lessened non-specific byproducts. In the present invention, the amplification process occurs spontaneously and isothermally under a broad range of conditions. The amplification reactions described below are a series of logical steps. The relative rate of each step will determine the effective yield of amplification product. Use of a mixture of blocked and unblocked primers reduces the side reactions, and hence improves amplification. Side products, such as "primer-dimers" have been described, and are well known in the art to affect the efficiency of amplification reactions. The present invention reduces the efficiency of formation of such byproducts, therefore enhancing amplification efficiency.

Suitable DNA polymerases for the present invention include reverse transcriptases such as avian myeloblastosis virus (AMV) reverse transcriptase and Moloney murine leukemia virus (MMLV) reverse transcriptase. Promoters or promoter sequences suitable for incorporation in promoter-primers used in the present invention are nucleic acid sequences (either naturally occurring, produced synthetically or by a restriction endonuclease digest) that are specifically recognized by an RNA polymerase that recognizes and binds to that sequence and initiates the process of transcription whereby RNA transcripts are produced. Promoter sequences for which there is a known and available polymerase that is capable of recognizing the initiation sequence are particularly suitable to be employed. Such promoters include those that are recognized by certain bacteriophage polymerases such as those from bacteriophage T3, T7 or SP6. The sequence may optionally include nucleotide bases extending beyond the actual recognition site for the RNA polymerase that may impart added stability or susceptibility to degradation processes or increased transcription efficiency.

Although some of the reverse transcriptases suitable for use in the present invention have an RNAse H activity, such as AMV or MMLV reverse transcriptase, it may be preferred to add exogenous RNAse H, such as E. coli RNAse H. For example, although the Examples (see below) show that the addition of exogenous RNAse H is not required, the RNAse H activity present in AMV reverse transcriptase may be inhibited by relatively large amounts of heterologous DNA present in the reaction mixture; one solution to the problem is to add exogenous RNAse H. Another instance when added RNAse H may be required is when an oligonucleotide hybridizes internally (i.e., the oligonucleotide hybridizes such that target sequence nucleotides extend past both the 3' and 5' ends of the oligonucleotide) on the target RNA.

The present invention does not require a denaturation step to separate the RNA-DNA complex produced by the first DNA extension reaction. Such denaturation steps require manipulation of reaction conditions such as by substantially increasing the temperature of the reaction mixture (generally from ambient temperature to about 80° C. to about 105° C.), reducing its ionic strength (generally by 10× or more) or changing pH (usually increasing pH to 10 or more). Such manipulations of the reaction conditions often deleteriously affect enzyme activities, requiring addition of additional enzyme and also necessitate further manipulations of the reaction mixture to return it to conditions suitable for further nucleic acid synthesis.

The second oligonucleotide in the mixture may be blocked or modified similarly to the first oligonucleotide. In one aspect of the present invention, if the first oligonucleotide is unmodified, then the second oligonucleotide is modified. Also, if the first oligonucleotide is not a promoter-primer, then the second oligonucleotide is a promoter-primer. Further, if the first oligonucleotide is only a primer, then it may be unblocked, and the second oligonucleotide is then a promoter-primer including both blocked and unblocked constituents consisting essentially of a single nucleic acid sequence.

Surprisingly, such a mixture of blocked and unblocked oligonucleotides consisting essentially of the same nucleic acid sequence reduces the amount of non-specific product formation, and thereby increases the effectiveness of the amplification.

The RNA copies or transcripts produced may autocatalytically multiply without further manipulation.

In another aspect of the present invention, the first and second oligonucleotides are both promoter-primers, and either or both may each consist of both modified and unmodified promoter-primers. In such a case, it is preferred that both promoters are recognized by the same RNA polymerase unless it is intended to introduce the second promoter for purposes other than amplification, such as cloning. Where both oligonucleotides are promoter-primers, then transcripts complementary to both strands of the double-stranded template will be produced during the autocatalytic reaction and the number of copies of the target sequence synthesized may be enhanced.

Note that, as the first oligonucleotide (primer or promoter-primer) defines one end of the target sequence, the second oligonucleotide (primer or promoter-primer) now defines the other end; the termini may also be defined by a specific restriction endonuclease, or by other suitable means (which may include a natural 3'-end). The RNA transcripts may have different termini from the original target nucleic acid, but the sequence between the first oligonucleotide and the second oligonucleotide remains intact. The RNA transcripts so produced may automatically recycle in the above system without further manipulation. Thus, this reaction is autocatalytic.

Also note that either oligonucleotide may have nucleotide sequences 5' to its priming sequence that can result in the addition of extra nucleotide sequence to the eventually resulting double stranded DNA; the extra nucleotide sequence is not limited to a promoter sequence.

In another embodiment, the present invention may consist of a first and second oligonucleotide in which a promoter-primer is provided which consists only of a blocked oligonucleotide, or only of an unblocked oligonucleotide, or an oligonucleotide with a mixture of different modifications at or near the 3'-end.

In further embodiments, the amplification is performed in the presence of additives to enhance amplification. Examples such as dimethyl sulfoxide, dimethyl formamide, ethylene glycol, glycerol or zinc have been used.

The components of the reaction mixture may be added stepwise or at once. The reaction advantageously takes place under conditions suitable for maintaining the stability of reaction components, such as the component enzymes, and without requiring modification or manipulation of reaction conditions during the course of the amplification reaction.

The present invention may be used as a component of assays to detect and/or quantitate specific nucleic acid target sequences in clinical, environmental, forensic, and similar samples or to produce large number of copies of DNA and/or RNA of specific target sequence for a variety of uses.

EXAMPLES

Preface

The following examples demonstrate the utility of the methods of the present invention. They are not limiting and should not be considered as such.

Unless otherwise specified the reaction conditions for amplification used in the following examples were 50 mM Tris-HCl, 35 mM KCl, 20 mM MgCl$_2$, 15 mM N-acetylcysteine, 4 mM rATP, 4 mM rCTP, 4 mM rGTP, 4 mM rUTP, 1 mM DATP, 1 mM dCTP, 1 mM dGTP, 1 mM dTTP, 10% glycerol, 10% dimethyl sulfoxide, 300–600 units MMLV reverse transcriptase, 200–400 units T7 RNA polymerase, 0.15 μM each primer or promoter-primer, and specified amounts of template and enzymes in 100 μl volumes at 42° C. for one hour. Dithiothreitol, spermidine and/or polyethyleneimine (PEI) may also advantageously be added to the reaction mixture.

The enzymes used in the following examples are T7 or T3 RNA polymerase and Moloney murine leukemia virus (MMLV) reverse transcriptase. Other RNA polymerases with different promoter specificities are also suitable.

The relative amplification was measured as follows. A sample of the amplification reaction mixture (usually 10 μl) was added to 100 μl of a luminescently labelled probe (for example, labelled with an acridinium ester—see HPA reference above) solution containing approximately 75 fmol probe, 0.1 M lithium succinate, pH 4.7, 2% (w/v) lithium lauryl sulfate, 15 mM aldrithiol, 20 mM EDTA, and 20 mM EGTA, and mixed. The reactions were then incubated 20 minutes at 60° C. and cooled. To each hybridization reaction was added 300 μl of 0.6 M sodium borate pH 8.5, 1% Triton X-100. The reactions were then mixed and incubated six minutes at 60° C. to destroy the chemiluminescent label of the unhybridized probe. This method of destruction of the chemiluminescent label of unhybridized probe is quite specific; only a very small fraction of the unhybridized probe remains chemiluminescent. The reactions were cooled and the remaining chemiluminescence was quantified in a luminometer upon the addition of 200 μl 0.1% hydrogen peroxide, 1 mM nitric acid, and surfactant, and 200 μl 1.0 N sodium hydroxide. In the assay, hybridized probe emits light. The quantity of photons emitted are measured in a luminometer and the results are reported as Relative Light Units or RLU. Since the reaction that destroys the chemiluminescent label of unhybridized probe is not 100% effective, there is generally a background level of signal present in the range of about 1000 to 2000 RLU.

Many other assay methods are also applicable, including assays employing hybridization to isotopically labeled probes, blotting techniques and electrophoresis.

These reaction conditions are not necessarily optimized, and have been changed as noted for some systems. The oligonucleotide sequences used are exemplary and are not meant to be limiting as other sequences have been employed for these and other target sequences.

Example 1

To show that amplification occurred with a modified promoter-primer complementary to a sequence within an RNA target, a promoter-primer complementary to a sequence within *M. tuberculosis* rRNA (Seq ID No. 1) was synthesized either unmodified or with a 3' alkane diol (RP) or 3' cordycepin (CO) and incubated with a primer of the same sense as the target RNA (Seq ID No. 2) and 3 tmol of target under the conditions described above. The reactions were analyzed with a probe of the same sense as the target RNA (Seq ID No. 3) with helper oligonucleotides as described in Hogan (U.S. Pat. No. 5,030,557, Means for Enhancing Nucleic Acid Hybridization, Seq ID Nos. 4 and 5). The results show that significant amplification does occur with a promoter-primer containing a 3' modification.

| Promoter-primer modification | RLU |
| --- | --- |
| Unmodified | 314,445 |
| 3' cordycepin | 71,382 |
| Unmodified | 683,737 |
| 3'-RP | 70,014 |

Example 2

In this experiment, a promoter-primer with a sequence complementary to *M. tuberculosis* 23S rRNA was modified by the presence of a 3' phosphorothioate nucleotide. Fifteen pmol of promoter-primer and primer (Seq ID Nos. 6 and 7) were used to amplify 0.3 tmol of target RNA, followed by detection with probe the same sense as the target RNA (Seq ID No. 8) with helper probes (Seq. ID Nos. 9 and 10). The results show that 3' phosphorothioate modified promoter-primer worked as well as unmodified oligonucleotide.

| Promoter-primer | RLU + target | RLU − target |
| --- | --- | --- |
| Unmodified | 2,614,079 | 899 |
| 3' phosphorothioate | 2,570,798 | 647 |

Example 3

To show that mixtures of modified and unmodified promoter-primers function in an amplification assay, reactions were performed with 15 pmol of the primer and a promoter-primer (see below) and assayed as described in Example 1. Three tmol of target RNA was used.

| | | Pmol Promoter-primer | | |
| --- | --- | --- | --- | --- |
| | | Unmodified | CO-modified | RLU |
| Experiment 1 | +Target | 15 | 0 | 834,902 |
| | +Target | 3 | 12 | 971,938 |
| | −Target | 3 | 12 | 1,456 |
| Experiment 2 | +Target | 3 | 12 | 1,015,199 |
| | +Target | 0.1 | 15 | 961,041 |

The results show that a mixture of blocked and unblocked oligonucleotides worked as well or better than all unblocked even at a ratio of 1:150 unblocked to blocked.

Example 4

In this experiment 3 tmol of target RNA were incubated with different concentrations of CO blocked and unblocked primer and a mixture of 15 pmol CO blocked promoter-primer and 0.1 pmol unblocked promoter-primer as in Example 1. Products were detected by hybridization assay.

| Pmol Primer | | |
| --- | --- | --- |
| Blocked | Unblocked | RLU |
| 0 | 15 | 969,522 |
| 10 | 5 | 802,840 |
| 13 | 2 | 648,271 |

In addition to the satisfactory amplification observed, it was surprisingly found that the amount of non-template directed product was significantly less in the reactions performed with blocked oligonucleotides compared to reactions performed with unblocked oligonucleotides.

Example 5

In this experiment, the effect of mixing a single oligonucleotide sequence with two different 3' modifications was demonstrated. Three tmol of target RNA was amplified as in Example 1. The promoter-primer was synthesized with an unblocked 3'-end, blocked with RP, or CO blocked. Two pmol of primer were used.

| Pmol Promoter-primer | | | |
|---|---|---|---|
| RP modified | CO modified | Unmodified | RLU |
| 0 | 15 | 0.1 | 450,157 |
| 2 | 13 | 0 | 678,871 |
| 5 | 10 | 0.01 | 681,647 |
| 5 | 10 | 0 | 755,839 |

This example shows that a mixture of unmodified and modified or a mixture of different types of modified promoter-primers amplified well, allowing detection of 3 tmol of RNA target in one hour.

Example 6

In this example, a mixture of modified and unmodified primers and promoter-primers were used to amplify 3 tmol *M. tuberculosis* rRNA. A mixture of 2 pmol RP-modified promoter-primer and 13 pmol of CO-modified promoter-primer were incubated with unmodified primer or a mixture of unmodified primer and primer synthesized with a 3' phosphorothioate nucleotide (PS). The sequences and hybridization probes are as in Example 1.

| Primer modification | | |
|---|---|---|
| Unmodified | PS modified | RLU |
| — | 15 pmol | 118,411 |
| 1 pmol | 14 pmol | 364,733 |
| No target | | 1,266 |

Under these conditions, the mixture of modified and unmodified primers work best.

Example 7

In this example, 80 tmol of *Neisseria gonorrhoeae* rRNA was amplified with a primer complementary to the rRNA (Seq. I.D. No. 13) and a mixture of 28 pmol 3'-RP blocked- and 2 pmol unblocked promoter primer of the same sense as the RNA target (Seq. I.D. No. 14). In some reactions, a 3'-blocked oligonucleotide (Seq. I.D. No. 15) capable of hybridizing to *N. gonorrhoeae* rRNA and forming an RNAse H substrate, was added to the amplification. An aliquot of the reactions was hybridized to an AE-labeled probe and two helper probes complementary to the rRNA sequence (Seq. I.D. Nos. 16, 17, and 18, respectively). RLU–RNAse H substrate oligo RLU+RNAse H substrate oligo.

| | |
|---|---|
| 7,910 | 32,473 |
| 16,337 | 728,246 |
| 17,304 | 80,487 |
| 12,518 | 51,893 |

Example 8

In this example, 3 or 30 tmol of *M. tuberculosis* rRNA was amplified with a primer (Seq. I.D. No. 7) and a mixture of 14 pmole of 3'-RP blocked- and 1 pmol unblocked promoter primer containing a promoter for T3 RNA polymerase (Seq. I.D. No. 19). The reaction was performed as in Example 1 except that 450 units of MMLV RT were used, 200 units of T3 RNA polymerase replaced the T7 RNA polymerase, and the reaction was terminated after 40 minutes.

| Target concentration | RLU value |
|---|---|
| 30 tmol | 358,053 |
| 3 tmol | 75,440 |
| 0 tmol | 553 |

The results demonstrate that a mixture of blocked and unblocked promoter primer can be used to amplify RNA using reverse transcriptase and T3 RNA polymerase.

Example 9

In this example, amplification of a DNA target with an RP modified promoter primer was examined. Three tmol of cloned HIV-1 DNA was incubated with 30 pmol of a primer with sequence 5'-ATAATCCACCTATCCCAGTAG-GAGAAAT-3' (SEQ. ID. NO. 20) and a promoter primer with sequence 5'-AATTTAATACGACTCACTATAGG-GAGACCACACCTTGTCTTATGTCCAGAATGCT-3' (SEQ. ID. NO. 21) at 95° C. for 5 minutes, then cooled to room temperature. After enzyme addition, the reaction was incubated at 37° C. for 2 hours. The conditions were 50 mM Tris-HCl, 40 mM potassium acetate pH 8, 18 mM $MgCl_2$, 5 mM DTT, 2 mM spermidine, 6.2 mM GTP, 6.2 mM ATP, 2 mM CTP, 2 mM UTP, 0.2 mM dTTP, 0.2 mM DATP, 0.2 mM dGTP, 0.2 mM dCTP, 800 U MMLV RT, 400 U T7 RNA polymerase. The promoter primer was unmodified or modified with an RP at the 3' end. The reactions were assayed with AE-labeled probe of the same sense as the primer. Results shown are the average of five replicates.

| Pmol' promoter primer | | |
|---|---|---|
| Unmodified | Modified | Average RLU |
| 30 | 0 | 127,223 |
| 26 | 4 | 411,692 |
| 0 | 30 | 743,877 |

It was unanticipated and surprising that amplification of a DNA target, especially one without a defined 3'-end, was not inhibited by the use of a modified promoter primer.

The present embodiments of this invention are to be considered in all respects as illustrative and not restrictive, the scope of the invention being indicated by the appended claims rather than by the foregoing description, and all changes which come within the meaning and range of equivalency of the claims therefore are intended to be embraced therein.

What is claimed is:

1. A kit for use in amplifying *Mycobacterium tuberculosis* nucleic acid, said kit containing:
   a first oligonucleotide comprising the nucleotide base sequence of xGCCGTCACCCCACCAACAAGCT (SEQ ID NO: 22); and a second oligonucleotide comprising the nucleotide base sequence of xGGGATAAGCCTGG-GAAACTGGGTCTAATACC (SEQ ID NO: 2), wherein x is nothing or is a sequence recognized by an RNA polymerase, and wherein each said oligonucleotide is from 22 to 100 bases in length.

2. An oligonucleotide for use in amplifying *Mycobacterium tuberculosis* nucleic acid, said oligonucleotide being from 22 to 100 nucleotide bases in length and comprising the nucleotide base sequence of xGCCGTCACCCCACCAA-CAAGCT (SEQ ID NO: 22) or a sequence of the same length and fully complementary thereto, wherein x is nothing or is a sequence recognized by an RNA polymerase.

3. A kit for use in amplifying and detecting *Mycobacterium tuberculosis* nucleic acid, said kit containing:

a first oligonucleotide of from 24 to 100 nucleotide bases in length and comprising the nucleotide base sequence of SEQ ID NO: 3; and a second oligonucleotide of from 22 to 100 nucleotide bases in length and comprising the nucleotide base sequence of xGCCGTCACCCCACCAACAAGCT (SEQ ID NO: 22) or xGGGATAAGCCTGG-GAAACTGGGTCTAATACC (SEQ ID NO: 2), wherein x is nothing or is a sequence recognized by an RNA polymerase.

4. A kit for use in amplifying and detecting *Mycrcobacterium tuberculosis* nucleic acid, said kit containing:

a first oligonucleotide of from 23 to 100 nucleotide bases in length and comprising the nucleotide base sequence of SEQ ID NO: 8; and a second oligonucleotide of from 20 to 100 nucleotide bases in length and comprising the nucleotide base sequence of xCCAGGCCACTTCCOCTAACC (SEQ ID NO: 23) or xCGCGGAACAGGCTAAACCG-CACGC (SEQ ID NO: 7), wherein x is nothing or is a sequence recognized by an RNA polymerase.

5. The kit of claim 3, wherein said second oligonucleotide has a 3' end which is modified to reduce or block extension of said second oligonucleotide by a polymerase.

6. The kit of claim 5 further comprising a third oligonucleotide having a 3' end which is unmodified, wherein said third oligonucleotide is from 20 to 100 nucleotide bases in length and comprises the nucleotide base sequence of xCCAGGCCACTTCCOCTAACC (SEQ TD NO: 23) or xCGCGGAACAGGCTAAACCGCACGC (SEQ ID NO: 7), wherein x is nothing or is a sequence recognized by an RNA polymerase, and wherein the nucleotide base sequences of said second and third oligonucleotides are different.

7. The oligonucleotide of claim 2, wherein said oligonucleotide has a 3' end which is modified to reduce or block extension of said oligonucleotide by a polymerase.

8. A composition comprising:

a first oligonucleotide in accordance with said oligonucleotide of claim 2, wherein said first oligonucleotide has a 3' end which is not modified to reduce or block extension of said first oligonucleotide by a polymerase; and a second oligonucleotide in accordance with said oligonucleotide of claim 2, wherein said second oligonucleotide has a 3' end which is modified to reduce or block extension of said second oligonucleotide by a polymerase.

9. The composition of claim 8 further comprising a third oligonucleotide having a 3' end which is modified to reduce or block extension by a polymerase, wherein the 3' ends of said second and third oligonucleotides are differently modified.

10. The kit of claim 4, wherein said second oligonucleotide has a 3' end which is modified to reduce or block extension of said second oligonucleotide by a polymerase.

11. The kit of claim 10 further comprising a third oligonucleotide having a 3' end which is not modified to reduce or block extension of said third oligonucleotide by a polymerase.

12. A primer oligonucleotide up to 100 nucleotide bases in length which hybridizes to a nucleotide base sequence region present in *Mycobacterium tuberculosis* nucleic acid under amplification reaction conditions, wherein the nucleotide base sequence of said region is selected from the group consisting of the nucleotide base sequences of SEQ ID NO: 22, the RNA equivalent thereof, and sequences of the same length and fully complementary thereto, and wherein said primer oligonucleotide includes an at least 10 contiguous nucleotide base sequence which is fully complementary to an at least 10 contiguous nucleotide base sequence contained within said region.

13. The primer oligonucleotide of claim 12, said primer being from 15 to 50 nucleotide bases in length.

14. The primer oligonucleotide of claim 12, wherein said primer oligonucleotide comprises a nucleotide base sequence of the same length and fully complementary to the nucleotide base sequence of said region.

15. The primer oligonucleotide of claim 12, wherein the nucleotide base sequence of said primer oligonucleotide consists of a nucleotide base sequence of the same length and fully complementary to the nucleotide base sequence of said region and, optionally, a sequence recognized by an RNA polymerase.

16. The primer oligonucleotide of claim 12 further comprising a sequence recognized by an RNA polymerase.

17. The primer oligonucleotide of claim 16, said primer oligonucleotide comprising the nucleotide base sequence of SEQ ID NO: 1.

18. The primer oligonucleotide of claim 16, wherein the nucleotide base sequence of said primer oligonucleotide consists of or is contained within the nucleotide base sequence of SEQ ID NO: 1.

19. A composition for use in amplifying *Mycobacterium tuberculosis* nucleic acid, said composition comprising:

a first primer oligonucleotide consisting of an oligonucleotide up to 100 nucleotide bases in length which hybridizes to a first nucleotide base sequence region present in *Mycobacterium tuberculosis* nucleic acid under amplification reaction conditions, wherein the nucleotide base sequence of said first region is selected from the group consisting of the nucleotide base sequences of SEQ ID NO:23, the RNA equivalent thereof, and sequences of the same length and fully complementary thereto, and wherein said first primer oligonucleotide includes an at least 10 contiguous nucleotide base sequence which is fully complementary to an at least 10 contiguous nucleotide base sequence contained within said first region; and a second primer oligonucleotide consisting of an oligonucleotide up to 100 nucleotide bases in length which hybridizes to a second nucleotide base sequence region present in *Mycobacterium tuberculosis* nucleic acid under amplification reaction conditions, wherein the nucleotide base sequence of said second region is selected from the group consisting of the nucleotide base sequences of SEQ ID NO: 7, the RNA equivalent thereof, and sequences of the same length and fully complementary thereto, and wherein said second primer oligonucleotide includes an at least 10 contiguous nucleotide base sequence which is fully complementary to an at least 10 contiguous nucleotide base sequence contained within said second region.

20. The composition of claim 19, wherein at least one of said first and second primer oligonucleotides further comprises a nucleotide base sequence which is recognized by an RNA polymerase which initiates transcription.

21. The composition of claim 19 further comprising a hybridization probe of from 10 to 100 nucleotide bases in length which hybridizes with specificity to at least 10 contiguous bases of a third nucleotide base sequence region present in *Mycobacterium tuberculosis* nucleic acid to form a detectable duplex under reaction conditions, wherein the nucleotide base sequence of said third region is selected from the group consisting of the nucleotide base sequences of SEQ ID NO: 8, the RNA equivalent thereof, and sequences ofihe same length and fully complementary thereto.

22. The composition of claim 21, wherein said probe comprises a nucleotide base sequence of the same length and fully complementary to the nucleotide base sequence of said third region.

23. The composition of claim 21, wherein said probe further comprises a detectable label.

24. The composition of claim 23, wherein said detectable label is an acridinium ester.

25. A composition for use in amplifying *Mycobacterium tuberculosis* nucleic acid, said composition comprising first and second primer oligonucleotides, each of said primer oligonucleotides being up to 100 nucleotide bases in length, wherein said first primer oligonucleotide hybridizes to a first nucleotide base sequence region present in *Mycobacterium tuberculosis* nucleic acid under amplification reaction conditions, and wherein the nucleotide base sequence of said first region is selected from the group consisting of the nucleotide base sequences of SEQ ID NO: 22, the RNA equivalent thereof, and sequences of the same length and fully complementary thereto, and wherein said first primer oligonucleotide includes an at least 10 contiguous nucleotide base sequence which is fully complementary to an at least 10 contiguous nucleotide base sequence contained within said first region, and wherein said second primer oligonucleotide hybridizes to a second nucleotide base sequence region present in *Mycobacterium tuberculosis* nucleic acid under amplification reaction conditions, and wherein the nucleotide base sequence of said second region is selected from the group consisting of the nucleotide base sequences of SEQ ID NO: 2, the RNA equivalent thereof, and sequences of the same length and fully complementary thereto, and wherein said second primer oligonucleotide includes an at least 10 contiguous nucleotide base sequence which is fully complementary to an at least 10 contiguous nucleotide base sequence contained within said second region.

26. The composition of claim 25, wherein:

said first primer oligonucleotide comprises a nucleotide base sequence of the same length and fully complementary to the nucleotide base sequence of said first region; and wherein said second primer oligonucleotide comprises a nucleotide base sequence of the same length and fully complementary to the nucleotide base sequence of said second region.

27. The composition of claim 25 or 26, wherein at least one of said first and second primer oligonucleotides further comprises a nucleotide base sequence which is recognized by an RNA polymerase which initiates transcription.

28. The composition of claim 25 or 26 further comprising a hybridization probe of from 10 to 100 nucleotide bases in length which hybridizes with specificity to at least 10 contiguous bases of a third nucleotide base sequence region present in *Mycobacterium tuberculosis* nucleic acid to form a detectable duplex under reaction conditions, wherein the nucleotide base sequence of said third region is selected from the group consisting of the nucleotide base sequences of SEQ ID NO: 3, the RNA equivalent thereof, and sequences of the same length and fully complementary thereto.

29. The composition of claim 26, wherein:

said first primer oligonucleotide comprises a nucleotide base sequence of the same length and fully complementary to the nucleotide base sequence of said first region;

said second primer oligonucleotide comprises a nucleotide base sequence of the same length and fully complementary to the nucleotide base sequence of said second region; and said probe comprises a nucleotide base sequence of the same length and fully complementary to the nucleotide base sequence of said third region.

30. The composition of claim 26, wherein said probe comprises a detectable label.

31. The composition of claim 30 wherein said detectable label is an acridinium ester.

32. A helper probe consisting essentially of a nucleotide sequence selected from the group consisting of SEQ ID NO:4 and SEQ ID NO:5.

33. A probe mix comprising:

a hybridization probe of from 10 to 100 nucleotide bases in length which hybridizes with specificity to at least 10 contiguous bases of a nucleotide base sequence region present in *Mycobacterium tuberculosis* nucleic acid to form a detectable hybridization duplex under reaction conditions, wherein the nucleotide base sequence of said region is selected from the group consisting of the nucleotide base sequences of SEQ ID NO: 8, the RNA equivalent thereof, and sequences of the same length and fully complementary thereto; and a helper oligonucleotide consisting essentially of a nucleic acid sequence selected from the group consisting of SEQ ID NO: 9 and SEQ ID NO: 10.

34. A probe mix comprising:

a hybridization probe of from 10 to 100 nucleotide bases in length which hybridizes with specificity to at least 10 contiguous bases of a nucleotide base sequence region present in *Mycobacterium tuberculosis* nucleic acid to form a detectable hybridization duplex under reaction conditions, wherein the nucleotide base sequence of said region is selected from the group consisting of the nucleotide base sequences of SEQ ID NO: 3, the RNA equivalent thereof, and sequences of the same length and fully complementary thereto; and a helper oligonucleotide consisting essentially of a nucleic acid sequence selected from the group consisting of SEQ ID NO: 4 and SEQ ID NO: 5.

35. A kit for use in amplifying *Mycobacterium tuberculosis* nucleic acid, said kit containing:

a first oligonucleotide comprising the nucleotide base sequence of xCCAGGCCACTTCCGCTAACC (SEQ ID NO: 23); and a second oligonucleotide comprising the nucleotide base sequence of xCGCGGAACAGGCTAAACCG-CACGC (SEQ ID NO: 7), wherein x is nothing or is a sequence recognized by an RNA polymerase.

36. A composition for use in detecting the presence of *Mycobacterium tuberculosis* in a sample, said composition comprising:

a) a hybridization probe of from 10 to 100 nucleotide bases in length comprising a nucleotide base sequence which hybridizes with specificity to at least 10 contiguous bases of a first nucleotide base sequence region present in *Mycobacterium tuberculosis* nucleic acid, wherein the nucleotide base sequence of said first region is selected from the group consisting of the nucleotide base sequences of SEQ ID NO: 3 and SEQ ID NO: 8, the RNA equivalents thereof, and sequences of the same length and fully complementary thereto; and b) a primer oligonucleotide of from 10 to 100 nucleotide bases in length which hybridizes to a second nucleotide base sequence region present in *Mycobacterium tuberculosis* nucleic acid under amplification reaction conditions, wherein the nucleotide base sequence of said second region is selected from the group consisting of the nucleotide base sequences of SEQ ID NO: 2, SEQ ID NO: 7, SEQ ID NO: 22 and SEQ ID NO: 23, the RNA equivalents thereof, and sequences of the same length and fully complementary thereto.

37. A composition comprising:

a first oligonucleotide comprising a first primer sequence able to hybridize at or near the 3' end of a (+) target nucleic acid sequence, a 5' promoter sequence, and a modification at or near the 3' end of said first primer sequence which reduces or blocks extension of said first primer sequence by a polymerase compared to said first primer sequence not having said modification;

a second oligonucleotide comprising a second primer sequence able to hybridize at or near the 3' end of said (+) target sequence, a 5' promoter sequence, and an optionally present modification at or near the 3' end of said second primer sequence which reduces or blocks extension of said second primer sequence by a polymerase compared to said second primer sequence not having said modification, wherein said second oligonucleotide hybridizes to said (+) target sequence in effectively the sane position as said first oligonucleotide, and wherein said modification to said second primer sequence, if present, is different than said modification to said first primer sequence;

a third oligonucleotide comprising a third primer sequence able to hybridize to the 3' end of a (−) target nucleic acid sequence which is the complement of said (+) target sequence, an optionally present 5' promoter sequence, and an optionally present modification at or near the 3' end of said third primer sequence which reduces or blocks extension of said third primer sequence by a polymerase compared to said third primer sequence not having said modification;

an enzyme selected from the group consisting of a DNA-dependent DNA polymerase and an RNA-dependent DNA polymerase; and one or more RNA polymerases that recognize said promoter sequence of said first and second oligonucleotides.

38. The composition of claim 37, wherein said (+) target sequence is RNA.

39. The composition of claim 37, wherein said composition further comprises RNAse H activity.

40. The composition of claim 39, wherein said RNAse H activity is supplied by an exogenous RNAse H from *E. coli*.

41. The composition of claim 39, wherein said RNAse H activity is supplied by a reverse transcriptase.

42. The composition of claim 37, wherein said enzyme is a reverse transcriptase which is both a DNA-dependent DNA polymerase and an RNA-dependent DNA polymerase.

43. The composition of claim 37 further comprising a molecule selected from the group consisting of DMSO, dimethylformamide, ethylene glycol, zinc and glycerol.

44. The composition of claim 37 further comprising a helper oligonucleotide.

45. The composition of claim 37, wherein said first and said second oligonucleotides are present in a molar ratio of between 1:1 and 1000:1.

46. The composition of claim 37, wherein said second primer sequence comprises said modification at or near its 3' end.

47. The composition of claim 46 further comprising a fourth oligonucleotide comprising a fourth primer sequence that hybridizes in effectively the same position as said first and second oligonucleotides and an optionally present 5' promoter sequence, wherein said fourth primer sequence does not contain a modification at or near its 3' end which reduces or blocks extension of said fourth primer sequence.

48. The composition of claim 46, wherein the 3' end modifications to said first and second primer sequences are independently selected from the group consisting of an alkane dial modification, a 3' deoxynucleotide residue, a nucleotide with a nonphosphodiester linkage, a non-nucleotide modification, a base non-complementary to said target sequence, and a dideoxynucleotide.

49. The composition of claim 46, wherein the 3' end modifications to said first and second primer sequences are independently selected from the group consisting of cordycepin, a ribonucleotide, and a phosphorothioate nucleotide.

50. The composition of claim 37, wherein said third primer sequence does not comprise said modification at or near its 3' end.

51. The composition of claim 37, wherein said third oligonucleotide comprises said 5' promoter sequence.

52. The composition of claim 51, wherein said third primer sequence comprises said modification at or near its 3' end.

53. The composition of claim 37, wherein said first and second primer sequences are the same.

54. The composition of claim 37, wherein said first and second primer sequences are different.

55. A composition comprising:

a first oligonucleotide comprising a first primer sequence able to hybridize to the 3' end of a (+) target nucleic acid sequence, an optionally present 5' promoter sequence, and an optionally present modification at or near the 3' end of said first primer sequence which reduces or blocks extension of said first primer sequence by a polymerase compared to said first primer sequence not having said modification;

a second oligonucleotide comprising a second primer sequence able to hybridize at or near the 3' end of a (−) target nucleic acid sequence which is the complement of said (+) target sequence, a 5' promoter sequence, and a modification at or near the 3' end of said second primer sequence which reduces or blocks extension of said second primer sequence by a polymerase compared to said second primer sequence not having said modification;

a third oligonucleotide comprising a third primer sequence able to hybridize at or near the 3' end of said (−) target sequence, a 5' promoter sequence, and an optionally present modification at or near the 3' end of said third primer sequence which reduces or blocks extension of said third primer sequence by a polymerase compared to said third primer sequence not having said modification, wherein said third oligonucleotide hybridizes to said (−) target sequence in effectively the same position as said second oligonucleotide, and wherein said modification to said third oligonucleotide, if present, is different than said modification to said second oligonucleotide;

an enzyme selected from the group consisting of DNA-dependent DNA polymerase and RNA-dependent DNA polymerase; and one or more RNA polymerases that recognize said promoter sequences of said first and second oligonucleotides.

56. The composition of claim 55, wherein said (+) target sequences RNA.

57. The composition of claim 55, wherein said composition further comprises RNAse H activity.

58. The composition of claim 57, wherein said RNAse H activity is supplied by an exogenous RNAse H from *E. coli*.

59. The composition of claim 57, wherein said RNAse H activity is supplied by a reverse transcriptase.

60. The composition of claim 55, wherein said enzyme is a reverse transcriptase which is both a DNA-dependent DNA polymerase and an RNA-dependent DNA polymerase.

61. The composition of claim 55 further comprising a molecule selected from the group consisting of DMSO, dimethylformamide, ethylene glycol, zinc and glycerol.

62. The composition of claim 55 further comprising a helper oligonucleotide.

63. The composition of claim 55, wherein said second and said third oligonucleotides are present in a molar ratio of between 1:1 and 1000:1.

64. The composition of claim 55, wherein said third primer sequence comprises said modification at its 3' end.

65. The composition of claim 64 further comprising a fourth oligonucleotide comprising a fourth primer sequence that hybridizes in effectively the same position as said second and third oligonucleotides and an optionally present 5' promoter sequence, wherein said fourth primer sequence does not comprise a modification at or near its 3' end which reduces or blocks primer extension of said fourth primer sequence.

66. The composition of claim 64, wherein said 3' end modifications to said second and third primer sequences are independently selected from the group consisting of an alkane diol modification, a 3' deoxynucleotide residue, a nucleotide with a nonphosphodiester linkage, a non-nucleotide modification, a base non-complementary to said target sequence, and a dideoxynucleotide.

67. The composition of claim 64, wherein the 3' end modifications to said second and third primer sequences are independently selected from the group consisting of cordycepin, a ribonucleotide, and a phosphorothioate nucleotide.

68. The composition of claim 55, wherein said first primer sequence does not comprise said modification at or near its 3' end.

69. The composition of claim 55, wherein said first oligonucleotide comprises said 5' promoter sequence.

70. The composition of claim 55, wherein said first primer sequence comprises said modification at or near its 3' end.

71. The composition of claim 69, wherein said promoter sequences of said first, second and third oligonucleotides are the same.

72. The composition of claim 55, wherein said promoter sequences of said second and third primer sequences are the same.

73. The composition of claim 55, wherein said promoter sequences of said second and said third primer sequences are different.

74. A kit comprising:
a first oligonucleotide comprising a first primer sequence able to hybridize at or near the 3' end of a (+) target nucleic acid sequence, a 5' promoter sequence, and a modification at or near the 3' end of said first primer sequence which reduces or blocks extension of said first primer sequence by a polymerase compared to said first primer sequence not having said modification;

a second oligonucleotide comprising a second primer sequence able to hybridize at or near the 3' end of said (+) target sequence, a 5' promoter sequence, and an optionally present modification at or near the 3' end of said second primer sequence which reduces or blocks extension of said second primer sequence by a polymerase compared to said second primer sequence not having said modification, wherein said second oligonucleotide hybridizes to said (+) target sequence in effectively the same position as said first oligonucleotide, and wherein said modification to said second primer sequence, if present, is different than said modification to said first primer sequence;

a third oligonucleotide comprising a third primer sequence able to hybridize to the 3' end of a (−) target nucleic acid sequence which is the complement of said (+) target sequence, an optionally present 5' promoter sequence, and an optionally present modification at or near the 3' end of said third primer sequence which reduces or blocks extension of said third primer sequence by a polymerase compared to said third primer sequence not having said modification;

an enzyme selected from the group consisting of DNA-dependent DNA polymerase and RNA-dependent DNA polymerase; and one or more RNA polymerases that recognize said promoter sequences of said first and second oligonucleotides.

75. The kit of claim 74 further comprising a hybridization probe able to indicate the presence of said (+) target sequence or said (−) target sequence.

76. A kit comprising:
a first oligonucleotide comprising a first primer sequence able to hybridize to the 3' end of a (+) target nucleic acid sequence, an optionally present 5' promoter sequence, and an optionally present modification at or near the 3' end of said first primer sequence which reduces or blocks extension of said first primer sequence by a polymerase compared to said first primer sequence not having said modification, a second oligonucleotide comprising a second primer sequence able to hybridize at or near the 3' end of a (−) target nucleic acid sequence which is the complement of said (+) target sequence, a 5' promoter sequence, and a modification at or near the 3' end of said second primer sequence which reduces or blocks extension of said second primer sequence by a polymerase compared to said second primer sequence not having said modification;

a third oligonucleotide comprising a third primer sequence able to hybridize at or near the 3' end of said (−) target sequence, a 5' promoter sequence, and an optionally present modification at or near the 3' end of said third primer sequence which reduces or blocks extension of said third primer sequence by a polymerase compared to said third primer sequence not having said modification, wherein said third oligonucleotide hybridizes to said (−) target sequence in effectively the same position as said second oligonucleotide and said modification to said third oligonucleotide, if present, is different than said modification to said second oligonucleotide;

an enzyme selected from the group consisting of DNA-dependent DNA polymerase and RNA-dependent DNA polymerase; and one or more RNA polymerases that recognize said promoter sequences of said first and second oligonucleotides.

77. The kit of claim 76 further comprising a hybridization probe able to indicate the presence of said (+) target sequence or said (−) target sequence.

78. An oligonucleotide for use in amplifying *Mycobacterium tuberculosis* nucleic acid, said oligonucleotide being from 20 to 100 nucleotide bases in length and comprising the nucleotide base sequence of xCCAGGCCACTTC-CGCTAACC (SEQ ID NO: 23) or a sequence of the same length and fully complementary thereto, wherein x is nothing or a sequence recognized by an RNA polymerase.

79. The composition of claim 78, wherein said oligonucleotide has a 3' end which is modified to reduce or block extension of said oligonucleotide by a polymerase.

80. A composition comprising:
a first oligonucleotide having a 3' end which is not modified to reduce or block extension of said first oligonucleotide by a polymerase; and
a second oligonucleotide having a 3' end which is modified to reduce or block extension of said second oligonucleotide by a polymerase, wherein each of said first and second oligonucleotides comprises a nucleotide base sequence selected from the group consisting of the nucleotide base sequences of xCCAGGCCACTTC-CGCTAACC (SEQ ID NO: 23), xCGCGGAACAG-GCTAAACCGCACGC (SEQ ID NO: 7), and sequences of the same length and fully complementary thereto, wherein x is nothing or a sequence recognized by an RNA polymerase.

81. The composition of claim 80 further comprising a third oligonucleotide having a 3' end which is modified to reduce or block extension of said third oligonucleotide by a polymerase, wherein the 3' ends of said second and third oligonucleotides are differently modified.

82. A primer oligonucleotide up to 100 nucleotide bases in length which hybridizes to a nucleotide base sequence region present in *Mycobacterium tuberculosis* nucleic acid under amplification reaction conditions, wherein the nucleotide base sequence of said region is selected from the group consisting of the nucleotide base sequences of SEQ ID NO: 23, the RNA equivalent thereof, and sequences of the same length and fully complementary thereto, and wherein said primer oligonucleotide includes an at least 10 contiguous nucleotide base sequence which is fully complementary to an at least 10 contiguous nucleotide base sequence contained within said region.

83. The primer oligonucleotide of claim 82, wherein said primer oligonucleotide is from 15 to 50 nucleotide bases in length.

84. The primer oligonucleotide of claim 82, wherein said primer oligonucleotide is from 20 to 100 nucleotide bases in length.

85. The primer oligonucleotide of claim 14, wherein said primer oligonucleotide is from 22 to 100 nucleotide bases in length.

86. The primer oligonucleotide of claim 82, wherein said primer oligonucleotide comprises a nucleotide base sequence of the same length and fully complementary to the nucleotide base sequence of said region.

87. The primer oligonucleotide of claim 82, wherein the nucleotide base sequence of said primer oligonucleotide is of the same length and fully complementary to the nucleotide base sequence of said region and, optionally, a sequence recognized by an RNA polymerase.

88. The primer oligonucleotide of claim 82 further comprising a nucleotide base sequence which is recognized by an RNA polymerase which initiates transcription.

89. The primer oligonucleotide of claim 88, wherein said primer oligonucleotide comprises the nucleotide base sequence of SEQ ID NO: 6 or SEQ ID NO: 19.

90. The primer oligonucleotide of claim 88, wherein the nucleotide base sequence of said primer oligonucleotide consists of or is contained within the nucleotide base sequence of SEQ ID NO: 6 or SEQ ID NO: 19.

91. The composition of claim 23 further comprising:
a first helper oligonucleotide comprising the nucleotide base sequence of SEQ ID NO: 9; and
a second helper oligonucleotide comprising the nucleotide base sequence of SEQ ID NO: 10.

92. The composition of claim 36 further comprising a helper oligonucleotide comprising a nucleotide base sequence selected from the group consisting of the nucleotide base sequences of SEQ ID NO: 4, SEQ ID NO: 5, SEQ ID NO: 9 and SEQ ID NO: 10, and sequences of the same length and fully complementary thereto.

93. A kit comprising a primer oligonucleotide up to 100 nucleotide bases in length which hybridizes to a nucleotide base sequence region present in *Mycobacterium tuberculosis* nucleic acid under amplification reaction conditions, wherein the nucleotide base sequence of said region is selected from the group consisting of the nucleotide base sequences of SEQ ID NO: 22 and SEQ ID NO: 23, the RNA equivalents thereof, and sequences of the same length and fully complementary thereto, and wherein said oligonucleotide primer includes an at least 10 contiguous nucleotide base sequence which is fully complementary to an at least 10 contiguous nucleotide base sequence contained within said region.

94. A composition for use in detecting the presence of *Mycobacterium tuberculosis* in a sample, said composition comprising:
a) a hybridization probe of from 10 to 100 nucleotide bases in length comprising a nucleotide base sequence which hybridizes with specificity to at least 10 contiguous bases of a first nucleotide base sequence region present in *Mycobacterium tuberculosis* nucleic acid under reaction conditions, wherein the nucleotide base sequence of said first region is selected from the group consisting of the nucleotide base sequences of SEQ ID NO: 3, the RNA equivalent thereof, and sequences of the same length and fully complementary thereto; and b) a primer oligonucleotide of from 10 to 100 nucleotide bases in length which hybridizes to a second nucleotide base sequence region present in *Mycobacterium tuberculosis* nucleic acid under amplification reaction conditions, wherein the nucleotide base sequence of said second region is selected from the group consisting the nucleotide base sequences of SEQ ID NO: 22 and SEQ ID NO: 2, the RNA equivalents thereof, and sequences of the same length and fully complementary thereto.

95. The composition of claim 94 further comprising a helper oligonucleotide comprising a nucleotide base sequence selected from the group consisting of the nucleotide base sequences of SEQ ID NO: 4 and SEQ ID NO: 5, and sequences of the same length and fully complementary thereto.

96. A kit comprising a primer oligonucleotide up to 100 nucleotide bases in length which hybridizes to a first nucleotide base sequence region present in *Mycobacterium tuberculosis* nucleic acid under amplification reaction conditions, wherein the nucleotide base sequence of said first region is selected from the group consisting of the nucleotide base sequences of SEQ ID NO: 22, the RNA equivalent thereof, and sequences of the same length and fully complementary thereto, and wherein said primer oligonucleotide includes an at least 10 contiguous nucleotide base sequence which is fully complementary to an at least 10 contiguous nucleotide base sequence contained within said first region.

97. A composition for use in detecting the presence of *Mycobacterium tuberculosis* in a sample, said composition comprising:

a) a hybridization probe of from 10 to 100 nucleotide bases in length comprising a nucleotide base sequence which hybridizes with specificity to at least 10 contiguous bases of a first nucleotide base sequence region present in *Mycobacterium tuberculosis* nucleic acid under reaction conditions, wherein the nucleotide base sequence of said first region is selected from the group consisting of the nucleotide base sequences of SEQ ID NO: 8, the RNA equivalent thereof, and sequences of the same length and fully complementary thereto; and b) a primer oligonucleotide of from 10 to 100 nucleotide bases in length which hybridizes to a second nucleotide base sequence region present in *Mycobacterium tuberculosis* nucleic acid under amplification reaction conditions, wherein the nucleotide base sequence of said second region is selected from the group consisting of the nucleotide base sequences of SEQ ID NO: 23 and SEQ ID NO: 7, the RNA equivalents thereof, and sequences of the same length and fully complementary thereto.

98. The composition of claim 97 further comprising a helper oligonucleotide comprising a nucleotide base sequence selected from the group consisting the nucleotide base sequences of SEQ ID NO: 9 and SEQ ID NO: 10, and sequences of the same length and fully complementary thereto.

99. A kit comprising a primer oligonucleotide up to 100 nucleotide bases in length which hybridizes to a nucleotide base sequence region present in *Mycobacterium tuberculosis* nucleic acid under amplification reaction conditions, wherein the nucleotide base sequence of said region is selected from the group consisting of the nucleotide base sequences of SEQ ID NO: 23, the RNA equivalent thereof, and sequences of the same length and fully complementary thereto, and wherein said primer oligonucleotide includes an at least 10 contiguous nucleotide base sequence which is fully complementary to an at least 10 contiguous nucleotide base sequence contained within said region.

100. A composition comprising a specifically detectable nucleic acid hybrid formed under reaction conditions between a nucleotide base sequence region present in *Mycobacterium tuberculosis* nucleic acid, or a sequence of the same length and fully complementary thereto, and a hybridization probe at least 10 nucleotide bases in length, wherein the entire nucleotide base sequence of said probe hybridizes with specificity to said region, or a sequence of the same length and fully complementary thereto, and wherein the nucleotide base sequence of said region is selected from the group consisting of the nucleotide base sequences of SEQ ID NO: 8, the RNA equivalent thereof, and sequences of the same length and fully complementary thereto.

101. The kit of claim 3 further comprising a helper oligonucleotide comprising a nucleotide base sequence selected from the group consisting of the nucleotide base sequences of SEQ ID NO: 4 and SEQ ID NO: 5, and sequences of the same length and fully complementary thereto.

102. The kit of claim 4 further comprising a helper oligonucleotide comprising a nucleotide base sequence selected from the group consisting of the nucleotide base sequences of SEQ ID NO: 9 and SEQ ID NO: 10, and sequences of the same length and fully complementary thereto.

103. The composition of claim 22, wherein said probe further comprises a detectable label.

104. The composition of claim 103, wherein said detectable label is an acridinium ester.

105. The composition of claim 103 further comprising:
a first helper oligonucleotide comprising the nucleotide base sequence of SEQ ID NO: 9; and
a second helper oligonucleotide comprising the nucleotide base sequence of SEQ ID NO: 10.

106. The kit of claim 96 further comprising a second primer oligonucleotide up to 100 nucleotide bases in length which hybridizes to a second nucleotide base sequence region present in *Mycobacterium tuberculosis* nucleic acid under amplification reaction conditions, wherein the nucleotide base sequence of said second region is selected from the group consisting of the nucleotide base sequences of SEQ ID NO: 2, the RNA equivalent thereof, and sequences of the same length and fully complementary thereto, and wherein said second primer oligonucleotide includes an at least 10 contiguous nucleotide base sequence which is fully complementary to an at least 10 contiguous nucleotide base sequence contained within said second region.

107. The kit of claim 99, wherein the nucleotide base sequence of said region is the nucleotide base sequence of SEQ ID NO: 23 or a sequence of the same length and fully complementary thereto.

108. A hybridization probe at least 10 nucleotide bases in length, wherein the entire nucleotide base sequence of said probe hybridizes with specificity to a nucleotide base sequence region present in *Mycobacterium tuberculosis* nucleic acid under reaction conditions, wherein the nucleotide base sequence of said region is selected from the group consisting of the nucleotide base sequences of SEQ ID NO: 8, the RNA equivalent thereof, and sequences of the same length and fully complementary thereto.

109. An oligonucleotide at least 20 bases in length, wherein the nucleotide base sequence of said oligonucleotide consists of or is contained within the nucleotide base sequence xCGCGGAACAGCTAAACCGCACGC (SEQ ID NO: 7) or a sequence of the same length and fully complementary thereto, wherein x is nothing or a sequence recognized by an RNA polymerase.

110. A kit comprising a primer oligonucleotide at least 10 nucleotide bases in length, wherein the entire nucleotide base sequence of said primer hybridizes to a nucleotide base sequence region present in *Mycobacterium tuberculosis* nucleic acid under amplification reaction conditions, wherein the nucleotide base sequence of said region is selected from the group of nucleotide base sequences of SEQ ID NO: 7, the RNA equivalent thereof, and sequences of the same length and fully complementary thereto.

111. The kit of claim 1, wherein each of said first and second oligonucleotides is up to 60 nucleotide bases in length.

112. The kit of claim 1, wherein:

the nucleotide base sequence of said first oligonucleotide consists of the nucleotide base sequence of SEQ ID NO: 22 and, optionally, a sequence recognized by an RNA polymerase; and the nucleotide base sequence of said second oligonucleotide consists of the nucleotide base sequence of SEQ ID NO: 2 and, optionally, a sequence recognized by an RNA polymerase.

113. The oligonucleotide of claim 2, wherein said oligonucleotide is up to 60 nucleotide bases in length.

114. The oligonucleotide of claim 2, wherein the nucleotide base sequence of said oligonucleotide consists of the nucleotide base sequence of SEQ ID NO: 22 and, optionally, a sequence recognized by an RNA polymerase.

115. The kit of claim 3, wherein:

the nucleotide base sequence of said first oligonucleotide consists of the nucleotide base sequence of SEQ ID NO: 3; and the nucleotide base sequence of said second oligonucleotide consists of the nucleotide base sequence of SEQ ID NO: 22 or SEQ ID NO: 2 and, optionally, a sequence recognized by an RNA polymerase.

116. The kit of claim 4, wherein:

the nucleotide base sequence of said first oligonucleotide consists of the nucleotide base sequence of SEQ ID NO: 8; and the nucleotide base sequence of said second oligonucleotide consists of the nucleotide base sequence of SEQ ID NO: 23 or SEQ ID NO: 7 and, optionally, a sequence recognized by an RNA polymerase.

117. The primer oligonucleotide of claim 18, wherein the nucleotide base sequence of said primer oligonucleotide consists of the nucleotide base sequence of SEQ ID NO: 1.

118. The composition of claim 19, wherein each of said first and second primer oligonucleotides is up to 60 nucleotide bases in length.

119. The composition of claim 19, wherein:

said first primer oligonucleotide comprises a nucleotide base sequence of the same length and fully complementary to the nucleotide base sequence of said first region; and said second primer oligonucleotide comprises a nucleotide base sequence of the same length and fully complementary to the nucleotide base sequence of said second region.

120. The composition of claim 19, wherein:

the nucleotide base sequence of said first primer oligonucleotide consists of a nucleotide base sequence of the same length and fully complementary to the nucleotide base sequence of said first region and, optionally, a sequence recognized by an RNA polymerase; and the nucleotide base sequence of said second primer oligonucleotide consists of a nucleotide base sequence of the same length and fully complementary to the nucleotide base sequence of said second region and, optionally, a sequence recognized by an RNA polymerase.

121. The composition of claim 19, wherein:

said first primer oligonucleotide comprises a nucleotide base sequence of the same length and fully complementary to the nucleotide base sequence of said first region;

said second primer oligonucleotide comprises a nucleotide base sequence of the same length and fully complementary to the nucleotide base sequence of said second region; and said probe comprises a nucleotide base sequence of the same length and fully complementary to the nucleotide base sequence of said third region.

122. The composition of claim 19, wherein:

the nucleotide base sequence of said first primer oligonucleotide consists of a nucleotide base sequence of the same length and fully complementary to the nucleotide base sequence of said first region and, optionally, a sequence recognized by an RNA polymerase;

the nucleotide base sequence of said second primer oligonucleotide consists of a nucleotide base sequence of the same length and fully complementary to the nucleotide base sequence of said second region and, optionally, a sequence recognized by an RNA polymerase; and the nucleotide base sequence of said probe consists of a nucleotide base sequence of the same length and fully complementary to the nucleotide base sequence of said third region.

123. The composition of claim 25, wherein each of said first and second primer oligonucleotides is up to 60 nucleotide bases in length.

124. The composition of claim 25, wherein:

the nucleotide base sequence of said first primer oligonucleotide consists of a nucleotide base sequence of the same length and fully complementary to the nucleotide base sequence of said first region and, optionally, a sequence recognized by an RNA polymerase; and the nucleotide base sequence of said second primer oligonucleotide consists of a nucleotide base sequence of the same length and fully complementary to the nucleotide base sequence of said second region and, optionally, a sequence recognized by an RNA polymerase.

125. The composition of claim 28, wherein:

the nucleotide base sequence of said first primer oligonucleotide consists of a nucleotide base sequence of the same length and fully complementary to the nucleotide base sequence of said first region and, optionally, a sequence recognized by an RNA polymerase;

the nucleotide base sequence of said second primer oligonucleotide consists of a nucleotide base sequence of the same length and fully complementary to the nucleotide base sequence of said second region and, optionally, a sequence recognized by an RNA polymerase; and the nucleotide base sequence of said probe consists of a nucleotide base sequence of the same length and fully complementary to the nucleotide base sequence of said third region.

126. The probe mix of claim 33, wherein said probe comprises a nucleotide base sequence of the same length and fully complementary to the nucleotide base sequence of said region.

127. The probe mix of claim 33, wherein the nucleotide base sequence of said probe is of the same length and fully complementary to the nucleotide base sequence of said region.

128. The probe mix of claim 34, wherein said probe comprises a nucleotide base sequence of the same length and fully complementary to the nucleotide base sequence of said region.

129. The probe mix of claim 34, wherein the nucleotide base sequence of said probe is of the same length and fully complementary to the nucleotide base sequence of said region.

130. The kit of claim 35, wherein:
the nucleotide base sequence of said first oligonucleotide consists of the nucleotide base sequence of SEQ ID NO: 23 and, optionally, a sequence recognized by an RNA polymerase; and
the nucleotide base sequence of said second oligonucleotide consists of the nucleotide base sequence of SEQ ID NO: 7 and, optionally, a sequence recognized by an RNA polymerase.

131. The composition of claim 36, wherein:
said probe comprises a nucleotide base sequence of the same length and fully complementary to the nucleotide base sequence of said first region; and
said primer oligonucleotide comprises a nucleotide base sequence of the same length and fully complementary to the nucleotide base sequence of said second region.

132. The composition of claim 36, wherein:
the nucleotide base sequence of said probe is of the same length and fully complementary to the nucleotide base sequence of said first region; and
the nucleotide base sequence of said primer oligonucleotide consists of a nucleotide base sequence of the same length and fully complementary to the nucleotide base sequence of said second region and, optionally, a sequence recognized by an RNA polymerase.

133. The oligonucleotide of claim 78, wherein said oligonucleotide is up to 60 nucleotide bases in length.

134. The composition of claim 78, wherein the nucleotide base sequence of said oligonucleotide consists of the nucleotide base sequence of SEQ ID NO: 23 and, optionally, a sequence recognized by an RNA polymerase.

135. The kit of claim 93, wherein said primer oligonucleotide is up to 60 nucleotide bases in length.

136. The kit of claim 93, wherein said primer oligonucleotide comprises a nucleotide base sequence of the same length and fully complementary to the nucleotide base sequence of said region.

137. The kit of claim 93, wherein the nucleotide base sequence of said primer oligonucleotide consists of a nucleotide base sequence of the same length and fully complementary to the nucleotide base sequence of said region and, optionally, a sequence recognized by an RNA polymerase.

138. The composition of claim 94, wherein:
said probe comprises a nucleotide base sequence of the same length and fully complementary to the nucleotide base sequence of said first region; and
said primer oligonucleotide comprises a nucleotide base sequence of the same length and fully complementary to the nucleotide base sequence of said second region.

139. The composition of claim 94, wherein:
the nucleotide base sequence of said probe is of the same length and fully complementary to the nucleotide base sequence of said first region; and
the nucleotide base sequence of said primer oligonucleotide consists of a nucleotide base sequence of the same length and fully complementary to the nucleotide base sequence of said second region and, optionally, a sequence recognized by an RNA polymerase.

140. The kit of claim 96, wherein said primer oligonucleotide is up to 60 nucleotide bases in length.

141. The kit of claim 96, wherein said primer oligonucleotide comprises a nucleotide base sequence of the same length and fully complementary to the nucleotide base sequence of said first region.

142. The kit of claim 96, wherein the nucleotide base sequence of said primer oligonucleotide consists of a nucleotide base sequence of the same length and fully complementary to the nucleotide base sequence of said first region and, optionally, as sequence recognized by an RNA polymerase.

143. The composition of claim 97, wherein:
said probe comprises a nucleotide base sequence of the same length and fully complementary to the nucleotide base sequence of said first region; and
said primer oligonucleotide comprises a nucleotide base sequence of the same length and fully complementary to the nucleotide base sequence of said second region.

144. The composition of claim 97, wherein:
the nucleotide base sequence of said probe is of the same length and fully complementary to the nucleotide base sequence of said first region, and
the nucleotide base sequence of said primer oligonucleotide consists of a nucleotide base sequence of the same length and fully complementary to the nucleotide base sequence of said second region and, optionally, a sequence recognized by an RNA polymerase.

145. The kit of claim 99, wherein said primer oligonucleotide comprises a nucleotide base sequence of the same length and fully complementary to the nucleotide base sequence of said region.

146. The kit of claim 99, wherein the nucleotide base sequence of said primer oligonucleotide consists a nucleotide base sequence of the same length and fully complementary to the nucleotide base sequence of said region and, optionally, a sequence recognized by an RNA polymerase.

147. The composition of claim 100, wherein said probe comprises a nucleotide base sequence of the same length and fully complementary to the nucleotide base sequence of said region.

148. The composition of claim 100, wherein the nucleotide base sequence of said probe is of the same length and fully complementary to the nucleotide base sequence of said region.

149. The kit of claim 106, wherein each of said first and second primer oligonucleotides is up to 60 nucleotide bases in length.

150. The kit of claim 106, wherein:
said first primer oligonucleotide comprises a nucleotide base sequence of the same length and fully complementary to the nucleotide base sequence of said first region; and said second primer oligonucleotide comprises a nucleotide base sequence of the same length and fully complementary to the nucleotide base sequence of said second region.

151. The kit of claim 106, wherein:
the nucleotide base sequence of said first primer oligonucleotide consists of a nucleotide base sequence of the same length and fully complementary to the nucleotide base sequence of said first region and, optionally, a sequence recognized by an RNA polymerase; and
the nucleotide base sequence of said second primer oligonucleotide consists of a nucleotide base sequence of the same length and fully complementary to the nucleotide base sequence of said second region and, optionally, a sequence recognized by an RNA polymerase.

152. The probe of claim 108, wherein said probe comprises a nucleotide base sequence of the same length and fully complementary to the nucleotide base sequence of said region.

153. The probe of claim 108, wherein the nucleotide base sequence of said probe is of the same length and fully complementary to the nucleotide base sequence of said region.

154. The oligonucleotide of claim 109, wherein the nucleotide base sequence of said oligonucleotide consists of the nucleotide base sequence of SEQ ID NO: 7.

155. The kit of claim 110, wherein said primer oligonucleotide comprises a nucleotide base sequence of the same length and fully complementary to the nucleotide base sequence of said region.

156. The kit of claim 110, wherein the nucleotide base sequence of said primer oligonucleotide is of the same length and fully complementary to the nucleotide base sequence of said region and, optionally, a sequence recognized by an RNA polymerase.

\* \* \* \* \*